United States Patent [19]
Yamasaki et al.

[11] Patent Number: 5,320,734
[45] Date of Patent: * Jun. 14, 1994

[54] TEST APPARATUS FOR MEASURING CONCENTRATION OF TEST SUBSTANCE IN LIQUID

[75] Inventors: Koichi Yamasaki, Oumihachiman; Tatsuhiko Osaka, Kurita; Hitonaga Nakano, Kouga; Toji Mukai, Yasu; Yasuhiro Nagata, deceased, late of Kusatsu, by Yuko Nagata, legal representative; Sadaaki Nakaoka, Osaka; Susumu Fujita, Tomiko Fujita, legal representative; Yoichi Hamada, both of Kobe, all of Japan

[73] Assignee: Daikin Industries, Ltd., Osaka, Japan

[*] Notice: The portion of the term of this patent subsequent to Jul. 20, 2010 has been disclaimed.

[21] Appl. No.: 968,470

[22] Filed: Oct. 29, 1992

Related U.S. Application Data

[63] Continuation of Ser. No. 448,116, Dec. 13, 1989, abandoned.

[30] Foreign Application Priority Data

Dec. 13, 1989 [JP] Japan .................. 63-314445
Dec. 13, 1989 [JP] Japan .................. 63-314447

[51] Int. Cl.$^5$ ................................. G01N 27/404
[52] U.S. Cl. ................ 204/415; 204/153.17; 204/279

[58] Field of Search .......... 204/153.17, 403, 415, 204/435, 279

[56] References Cited

U.S. PATENT DOCUMENTS

| | | | |
|---|---|---|---|
| 3,926,765 | 12/1975 | Haddad | 204/435 |
| 3,997,420 | 12/1976 | Buzza | 204/415 |
| 4,336,091 | 6/1982 | Gottermeier | 156/244.12 |
| 4,757,022 | 7/1988 | Shults et al. | 204/415 |
| 4,757,022 | 7/1988 | Shults et al. | 204/415 |
| 4,912,986 | 4/1990 | Marsoner et al. | 204/400 |
| 4,929,330 | 5/1990 | Osaka et al. | 204/415 |
| 4,933,066 | 6/1990 | Osaka et al. | 204/403 |

FOREIGN PATENT DOCUMENTS

WO88/07675 10/1988 PCT Int'l Appl.
WO89/04481 5/1989 PCT Int'l Appl.

Primary Examiner—T. Tung
Attorney, Agent, or Firm—Beveridge, DeGrandi, Weilacher & Young

[57] ABSTRACT

A test apparatus for measuring concentration of test solution, in which a thin sheet having a plurality of through holes and diffusion-limiting membranes to cover corresponding through hole, is movably installed, and one or two openings for deposition and a concentration measuring section are disposed in a thin sheet moving direction.

12 Claims, 26 Drawing Sheets

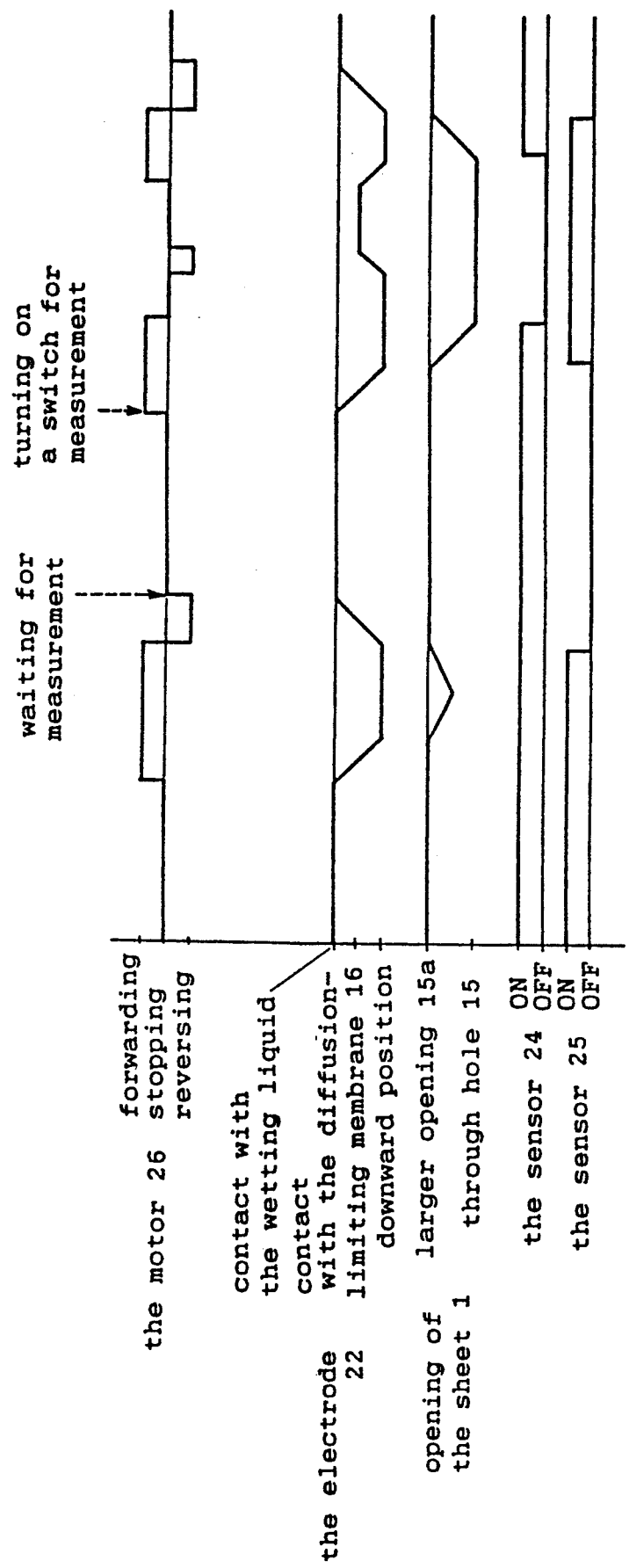

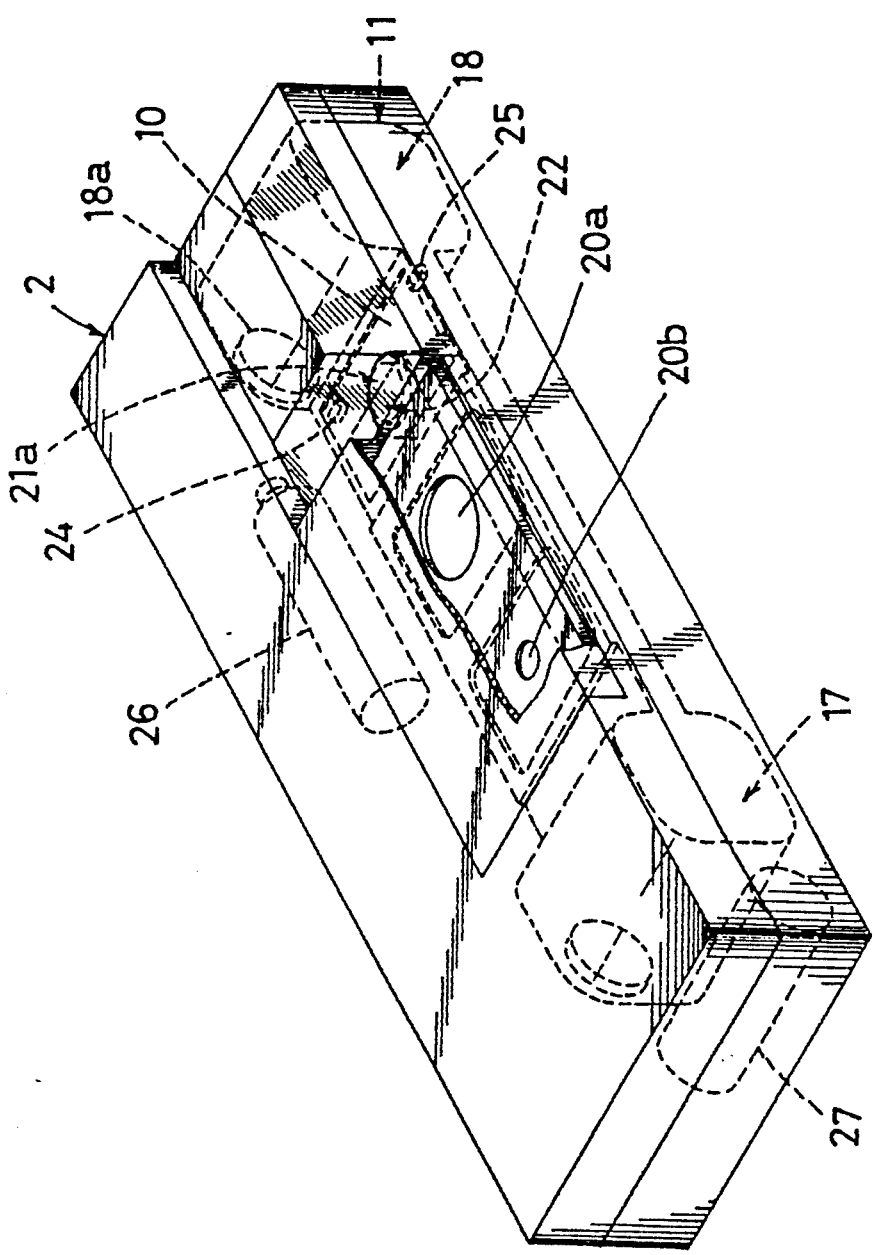

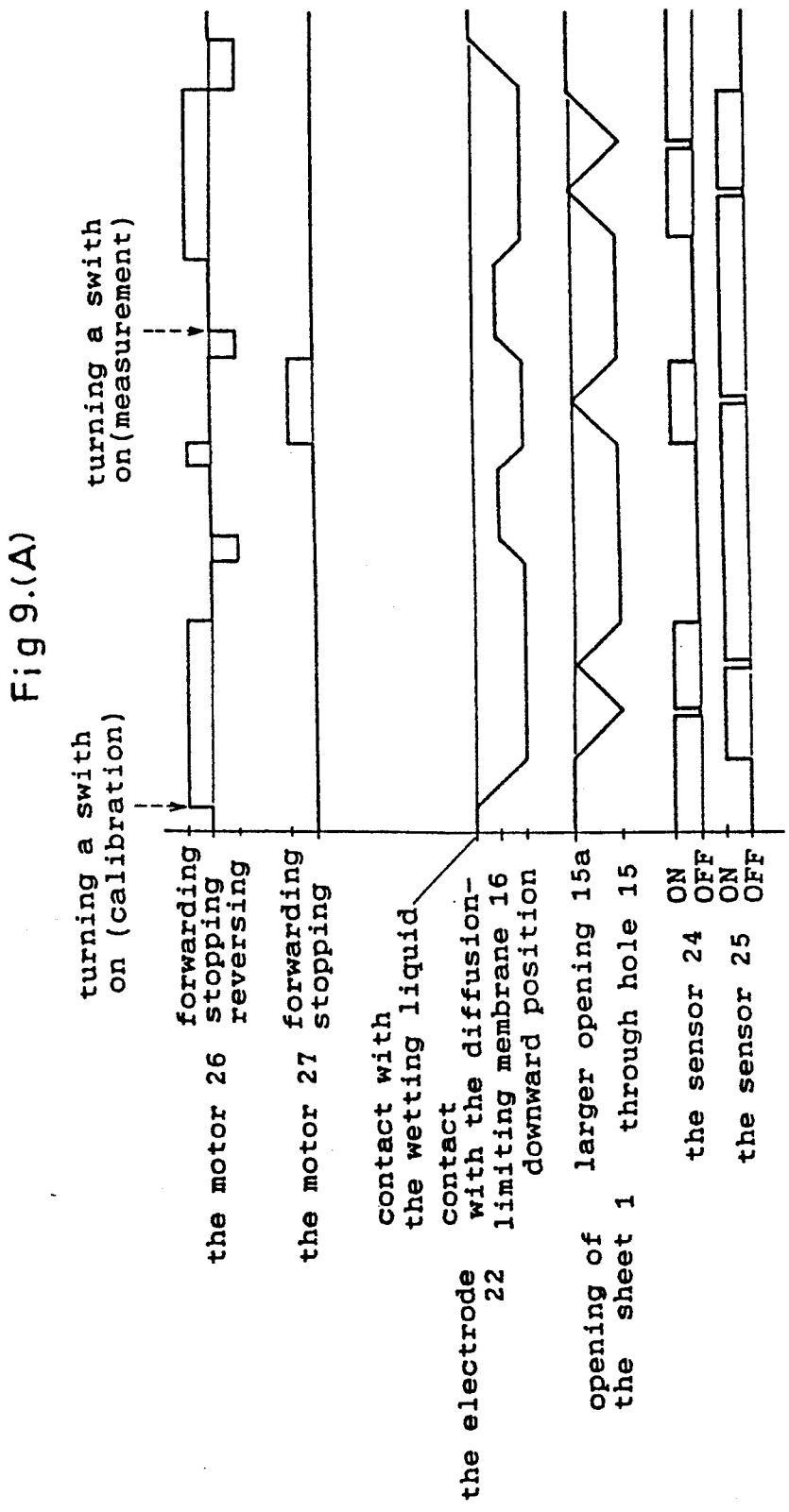

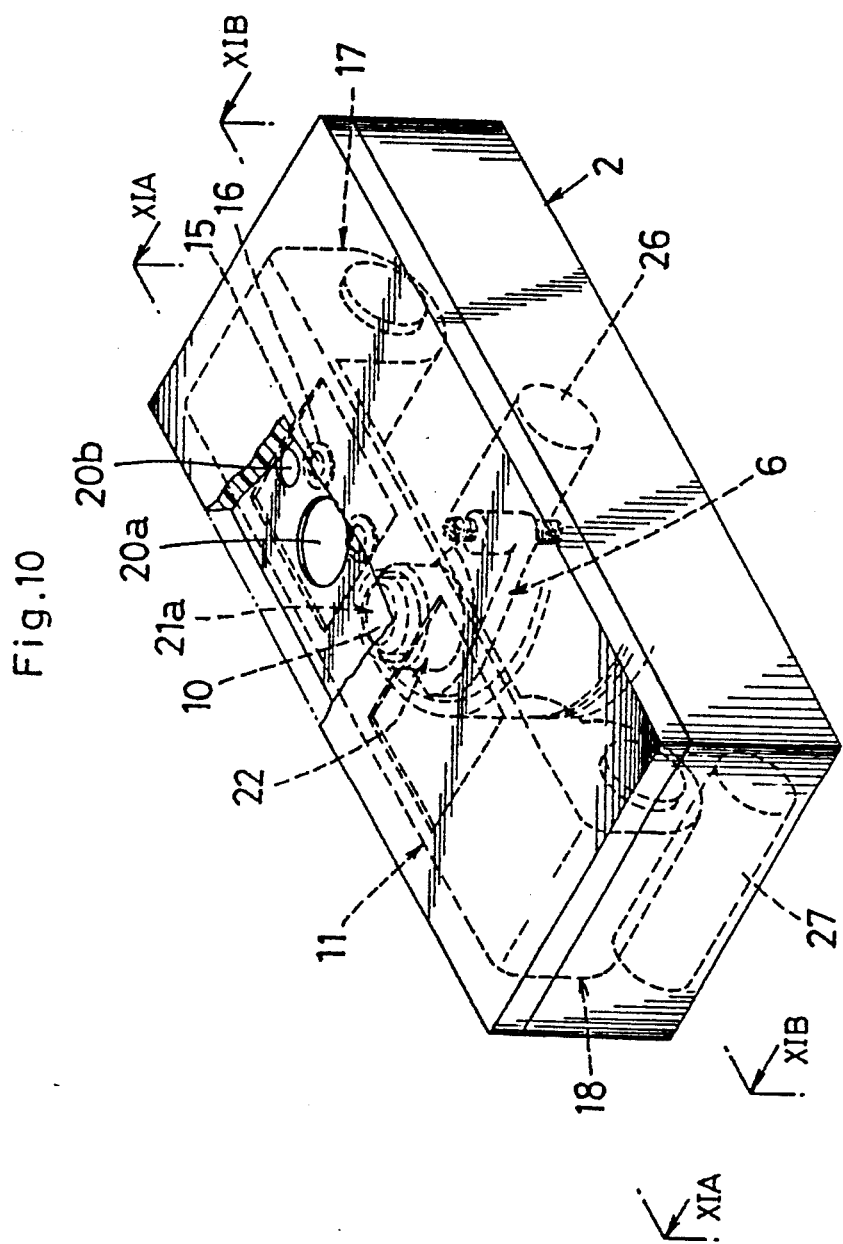

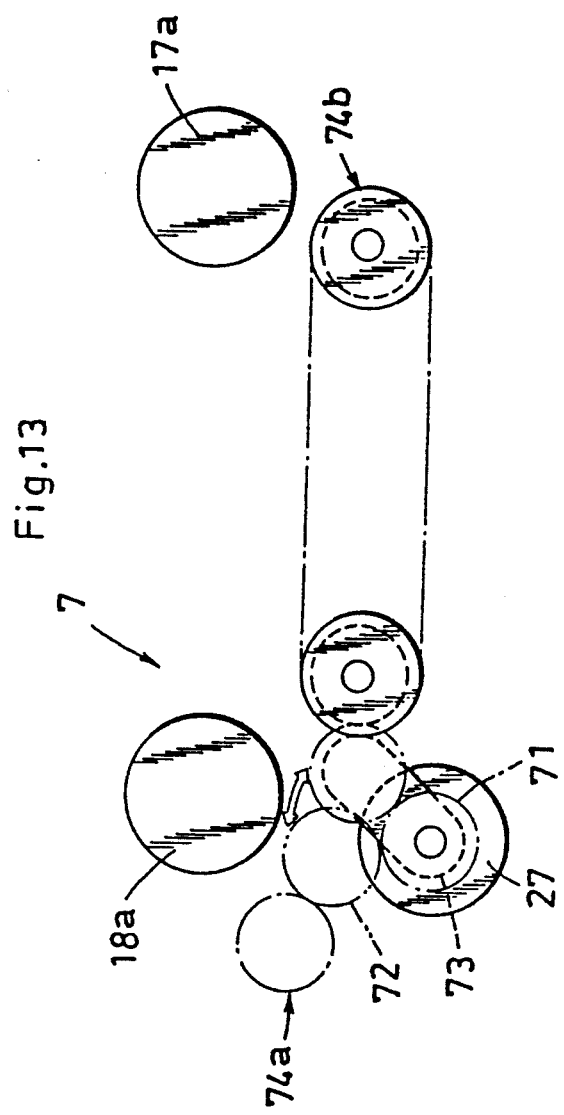

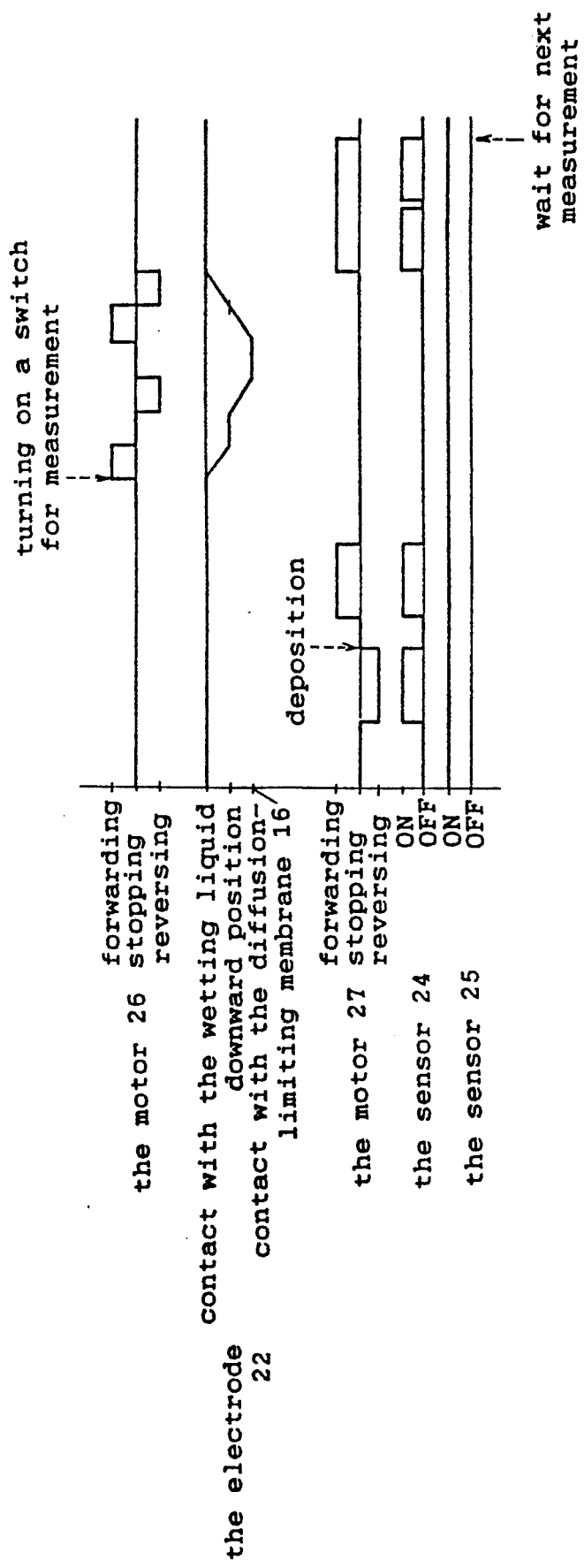

TEST APPARATUS FOR MEASURING CONCENTRATION OF TEST SUBSTANCE IN LIQUID

This application is a continuation of application Ser. No. 07/448,116, filed Dec. 13, 1989, now abandoned, which application is entirely incorporated herein by reference.

BACKGROUND OF THE INVENTION

1. Field of the Invention

This invention relates to a concentration measuring apparatus for measuring of test substance in liquid based on diffused substance which is diffused through a diffusion-limiting membrane.

2. Description of Related Arts

It is known that a physiologically active substance has a characteristic capable of selectively detecting a very complicated organic compound, protein or the like with high sensibility. With attention directed to this characteristic, research and development has been made on measurement of such organic compound, protein or the like with the use of an enzyme electrode unit having base electrodes on which a physiologically active substance (hereinafter referred to as an enzyme) is immobilized.

When measuring a test substance in a liquid with the use of the enzyme electrode unit above-mentioned, the test substance is oxidized or reduced in the presence of such enzyme. The concentration of the test substance is determined by measuring the amount of a substance produced or consumed in such oxidation or reduction. For instance when the concentration of glucose is measured with using an enzyme electrode consisting of a glucose oxidase as an enzyme and a platinum electrode and a silver electrode as base electrodes, the following reaction is occurring.

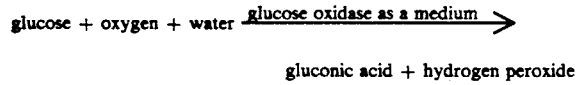

As is apparent from the reaction equation, oxygen is consumed and hydrogen peroxide is produced. So the concentration of glucose is determined by measuring the amount of produced hydrogen peroxide or consumed oxygen. The upper limit of concentration which can be measured, is accordingly determined dependent on the amount of a substance provoking such oxidation or reduction, for example the amount of oxygen.

In view of the foregoing, it has been proposed to increase the concentration measuring limit by limiting the penetration rate of a test substance by a diffusion-limiting membrane mounted on the surface of enzyme-immobilized membrane.

More specifically, there has been adopted an arrangement in which the diffusion-limiting membrane is mounted on a cap to be threadably secured to the base portion of a rod-like enzyme electrode unit, and screwing the cap into position causes the diffusion-limiting membrane to be automatically contacted with the enzyme-immobilized membrane.

With the use of such arrangement, the penetration rate of a test substance to be measured is limited by the diffusion-limiting membrane, thereby to achieve measurement of a considerably high concentration. That is, an output signal from the enzyme electrode is lowered by limiting the penetration rate of a test substance, but the output signal is hard to saturate notwithstanding the increase of concentration of a test substance in a liquid. And the concentration measuring limit is decided by the saturation point. As a result, the concentration measuring limit is increased up to the concentration corresponding to the saturation point. To eliminate the influence of interfering substances contained in a test solution to be measured (for example, increase in diffusion limiting effect resulting from the adhering of such interfering substances), the diffusion-limiting membrane needs to be replaceable. This is the reason for adopting the cap membrane screwing mechanism. (Japanese Patent Laid Open No. Sho 63-243863)

When the diffusion-limiting membrane holding means having the arrangement above-mentioned is used, replacement of the diffusion-limiting membrane may be relatively facilitated. There are instances, however, where it becomes very difficult to mount or remove the holding means on or from the base portion of an enzyme electrode unit due to the arrangement of its mounting mechanism, or where it is not possible to achieve a uniform contact of the diffusion-limiting membrane to the enzyme-immobilized membrane due to the degree of the screwing force.

Further, when the enzyme electrode unit base portion has a small diameter, resulting in decrease in the cap size, this causes the manual mounting/removal operation to be very difficult. This makes the problems above-mentioned more serious.

Moreover, the diffusion-limiting membrane is mounted on a cap, requiring a large space for preserving and/or transporting the same.

Considering the above points, it is proposed to employ a diffusion-limiting membrane holder which is constructed with a thin plate having a through hole and a diffusion-limiting membrane adhered to one side of the thin plate to cover the through hole, and measuring the concentration of test solution under the condition of pressure contacting the diffusion-limiting membrane to the surface of the enzyme electrode unit (refer to U.S. Pat. application Ser. No. 176,288). This causes the problems that dropping operation of solution including test substance (hereinafter referred to as test solution) to the through hole through the diffusion-limiting membrane is difficult and pressure contacting operation of the diffusion-limiting membrane to the surface of the enzyme electrode unit, and that quite a number of exchanging operations of the diffusion-limiting membrane holder are needed, and thereby the concentration measuring operation as a whole is complicated. Also, upon completion of the measurement as above-mentioned, a relatively great amount of interfering substances are stuck to the diffusion-limiting membrane. This inevitably degrades the diffusion limiting effect of the diffusion-limiting membrane which is to limit diffusion of a test substance to be measured. Therefore, the diffusion-limiting membrane as it is, cannot assure an accurate measurement on and after the second operation. It is accordingly a common practice that, after a predetermined number of measurements have been made, preferably after every measurement has been made, the diffusion-limiting membrane is exchanged with new one to achieve measurement without any influence of the interfering substances. As a result, a greater quantity of thin plate than would be needed for contacting the diffusion-limiting membrane must be used. Further, the disposal of used thin plate and picking out of new thin plates is needed. This complicates the series of operations to measure the concentration of the test substance.

More specifically, a series of operations is needed as follows:

(1) a power switch provided with the concentration measuring apparatus is turned on, (2) a cover provided with the concentration measuring apparatus is opened, (3) a package is opened and a thin plate on which a diffusion-limiting membrane is stuck is picked out, (4) test solution is dropped onto the thin plate (if test solution is blood, blood is drawn, then the blood is deposited onto the thin plate), (5) the thin plate is inserted into the concentration measuring apparatus, (6) the diffusion-limiting membrane adhered to the inserted thin plate is pressure contacted to the surface of the electrode for measuring concentration, then the concentration of the test substance is measured, (7) after measurement is made, the diffusion-limiting membrane is released from the surface of the electrode, (8) the thin plate is pulled out from the concentration measuring apparatus, (9) the cover provided with the concentration measuring apparatus is closed,

(10) the pulled out thin plate is disposed of and

(11) the power switch is turned off.

The series of operations is needed, and particularly time consuming operations are needed, thereby complicating concentration measuring operations as a whole. Further, the above-mentioned series of operations do not include a calibrating operation based on a standard solution having an established concentration of a test substance. In practice the calibrating operation is needed, so the operations are more complicated as a whole.

The description hereinbefore which has discussed mainly the case of concentration measuring of a test substance when using an enzyme electrode unit, may be applied to the case of concentration measuring of a test substance with using the other electrode unit, and may also cause similar problems.

SUMMARY OF THE INVENTION

It is an object of the present invention to simplify concentration measuring operation, while keeping an increased concentration measuring limit and an improved accuracy of concentration measurement.

It is another object of the present invention to decrease frequency of installing and removing operation of diffusion-limiting membrane to and from an electrode, while keeping an increased concentration measuring limit and an improved accuracy of concentration measurement.

It is a further object of the present invention to prevent infection resulting from disease germs from occurring.

In order to achieve the objects above-mentioned, the test apparatus for measuring concentration of test substance in a liquid in accordance with the present invention comprises:

a cartridge for housing diffusion-limiting membrane holding member which includes a thin sheet in which through holes for penetrating test solution therethrough are formed at every predetermined distance and diffusion-limiting membranes are adhered to the thin sheet to cover the corresponding through hole, movably in a predetermined direction; a casing for housing said cartridge therein in a removable manner;

a concentration measuring electrode provided with said casing;

depositing portion means for depositing test solution onto a through hole, said depositing portion means being formed at an upper portion of said casing; and concentration measuring portion means for contacting said concentration measuring electrode with a diffusion-limiting membrane, said concentration measuring portion means being formed at an upper portion of said casing, and being apart by a predetermined distance from said depositing portion means in a thin sheet moving direction.

The thin sheet may be an elongated sheet or a disk-shaped sheet. When an elongated sheet is employed, the sheet is movable in an elongated direction. When a disk-shaped sheet is employed, the sheet is movable in a rotating direction.

A sheet driving mechanism for moving the thin sheet in one direction may be provided to the casing, or a sheet driving mechanism for moving the thin sheet to and fro may be provided to the casing.

It is preferable that the depositing portion means is a larger opening than the through hole for penetrating test solution, and the depositing portion means and the concentration measuring portion means are apart by distance between neighboring through holes. The depositing portion means may not be an especially formed opening, but may be simply revealing the diffusion-limiting membrane holding member to a predetermined extent.

It is also preferable that two depositing portions means are provided a predetermined distance apart one the other to the casing, and a cover for covering any one of the depositing portion means selectively is provided to the casing. In this case, it is preferable that a smaller opening than the through hole is formed at a predetermined position of the cover, the smaller opening being possible to opposite to the through hole revealed through one of the depositing portion means.

It is preferable that two depositing portion means are provided a predetermined distance apart one the other to the casing, the predetermined distance corresponding with the distance between neighbouring through holes, and a lighting device is secured below the elongated sheet opposite to one of the depositing portion means.

It is also preferable that an electrode driving mechanism is further provided. The mechanism moves the concentration measuring electrode to and fro on a plane which is substantially parallel to a plane on which the diffusion-limiting membrane holding member moves, and moves the concentration measuring electrode up and down at a limit position of moving on the plane. The electrode driving mechanism may move the concentration measuring electrode to and fro in a direction which is not parallel to a moving direction of the thin sheet on the plane which is substantially parallel to a plane on which the diffusion-limiting membrane holding member moves, or the electrode driving mechanism may move the concentration measuring electrode to and fro in a direction which is parallel to a moving direction of the thin sheet on the plane which is substantially parallel to a plane on which the diffusion-limiting membrane holding member moves.

It is preferable that a wetting liquid housing member is further provided opposite to the concentration measuring electrode which is moved to a position not opposite to the concentration measuring portion means.

According to the test apparatus for measuring concentration of target substance in liquid having the arrangement above mentioned, first, the diffusion-limiting membrane holding member is housed in the predetermined position of the casing in a movable manner, second, test solution is deposited onto the through hole of the thin sheet for penetrating the test solution through the depositing portion means, third, the diffusion-limiting membrane is moved toward the concentration measuring portion means by a predetermined distance, fourth, the concentration measuring electrode is contacted with the diffusion-limiting membrane, thereby the concentration of test substance included in the test solution can be measured. As a result, installing and removing operation of diffusion-limiting membrane to and from is unnecessary during the number of measurements carried out, the number equals the number of through holes formed in the thin sheet. Additionally, infection resulting from disease germs is securely prevented from occuring even when test solution is body fluid, because the depositing portion means and concentration measuring portion means are apart one the other.

The above, and other objects, features and advantages of this invention will be apparent from the following detailed description of illustrative embodiments which is to be read in connection with the accompanying drawings.

BRIEF DESCRIPTION OF THE DRAWINGS

FIG. 6 is a timing chart explaining concentration measuring operation;

FIG. 7 is a partial cutaway perspective view of a test apparatus for measuring concentration of a test substance in liquid in accordance with a second embodiment of the present invention;

FIG. 10 is a partial cutaway perspective view of a test apparatus for measuring concentration of a test substance in liquid in accordance with a third embodiment of the present invention;

FIG. 13 is a diagram useful in understanding the operation of a thin sheet driving mechanism;

FIGS. 14A to 14C are timing charts explaining concentration measuring operation of the third embodiment;

DESCRIPTION OF THE PREFERRED EMBODIMENTS

Figure 1:
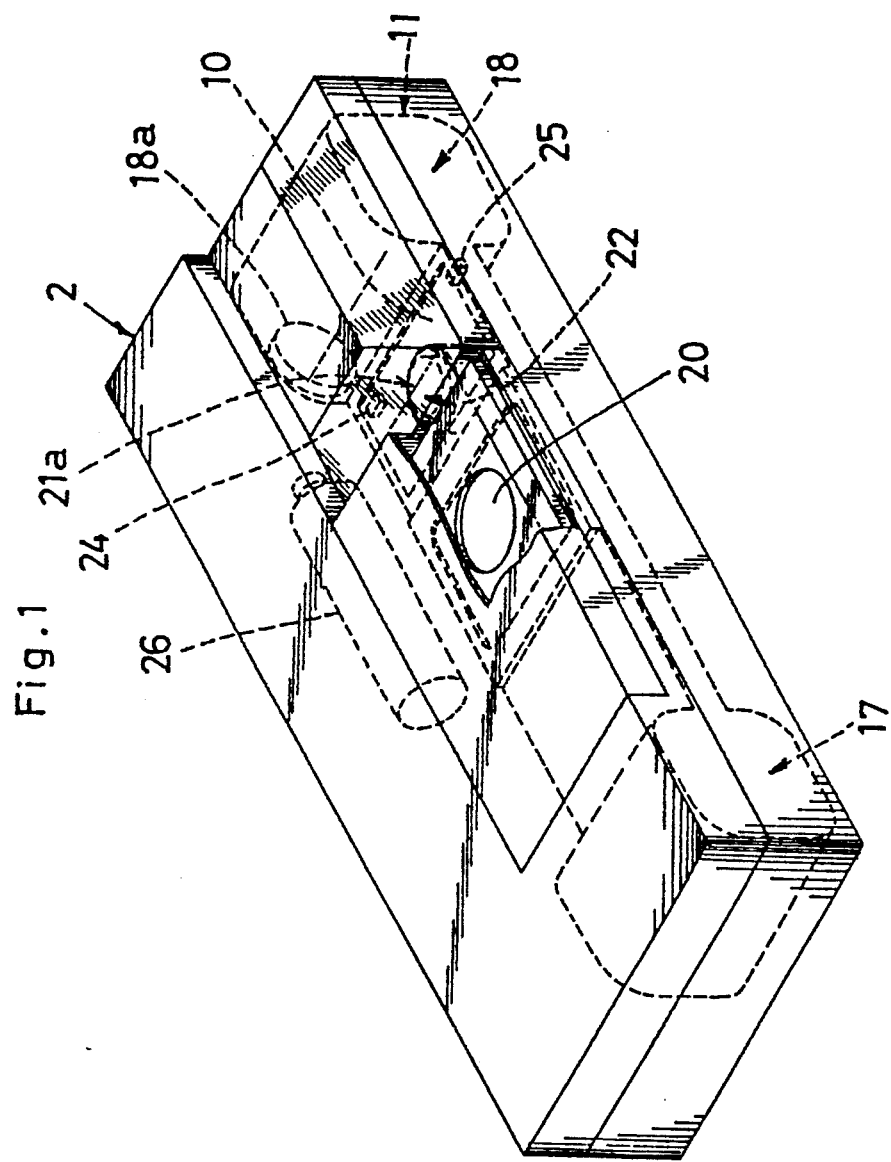
FIG. 1 is a partial cutaway perspective view of a test apparatus for measuring concentration of a test substance in liquid in accordance with a first embodiment of the present invention.
Figure 2:
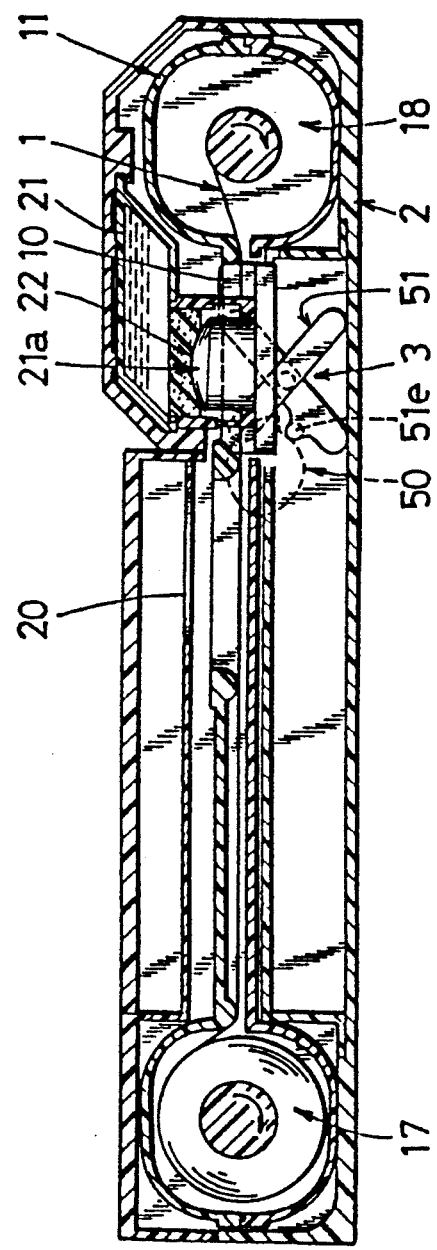
FIG. 2 is a vertical section view of the center portion of the test apparatus in FIG. 1.

FIG. 1 is a partial cutaway perspective view of a test apparatus in accordance with a first embodiment of the present invention, while FIG. 2 is a vertical section view of the center portion of the same.

In FIGS. 1 and 2, a cartridge 11 in which a thin elongated sheet 1 is housed, is housed in a predetermined position of a test apparatus casing. An opening 20 for deposition is formed at the upstream predetermined position of a thin elongated sheet moving path. A measuring portion 21a is formed at downstream-ward predetermined position of the thin elongated sheet moving path, and a wetting liquid housing tank 21 is positioned above the measuring portion 21a. A concentration measuring electrode driving mechanism 3 is provided in the test apparatus casing 2, the mechanism 3 elevates a concentration measuring electrode 22 to the contacting position with the thin elongated sheet 1 or contacting portion with the wetting liquid housing tank 21 selectively. A pair of sensors 24 and 25 are provided in the test apparatus casing 2, the sensor 24 being opposite to a positioning hole 13 or an end detecting hole 14 while the sensor 25 being opposite to a positioning hole 13a, the holes 13, 13a and 14 are formed in a predetermined position of the thin elongated sheet 1. Both sensors 24 and 25 are reflection-type photo sensors, and are activated simultaneously only when the end detecting hole is opposite to the sensor 24, otherwise, sensors 24 and 25 are never activated simultaneously. A motor 26 to generate driving force for elevating the concentration measuring electrode 22 and for moving the thin elongated sheet 1, is provided in the test apparatus casing 2. A processing section (not shown) for performing necessary processing and generating concentration data based on electrical signals outputted from the concentration measuring electrode 22, and a control section (not shown) for driving the motor 26 are provided in the test apparatus casing 2. Such processors are well known in the art.

Figure 3:
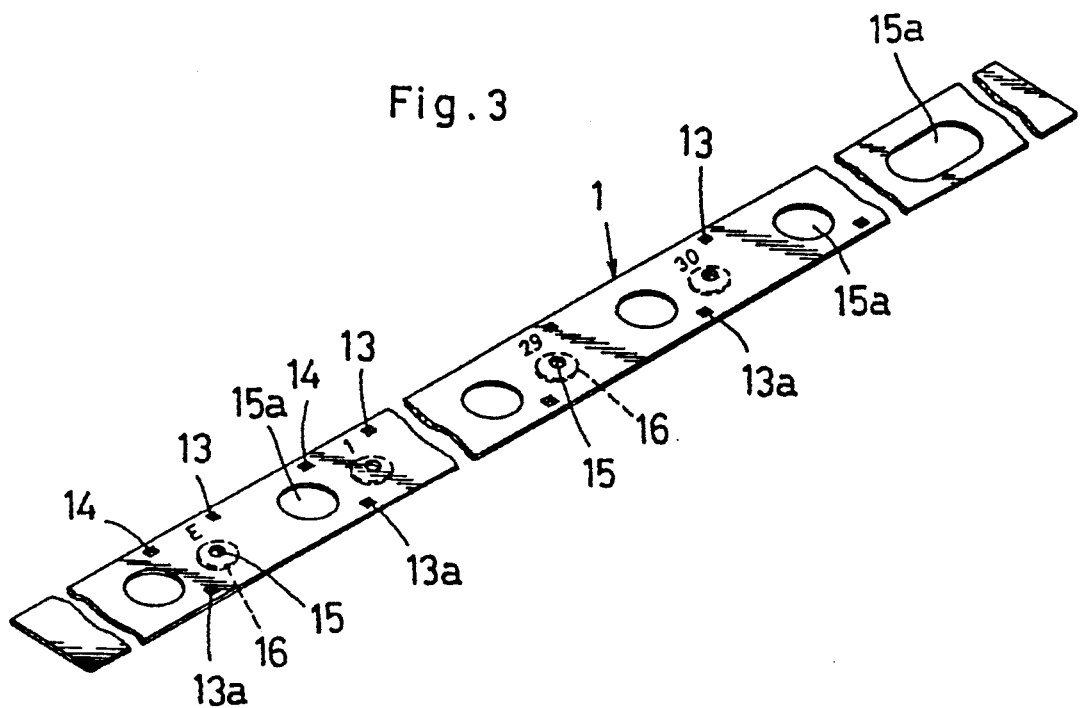
FIG. 3 is a perspective view of a diffusion-limiting membrane holding member.

FIG. 3 is a perspective view of the diffusion-limiting membrane holding member. A plurality of through holes 15 and larger openings 15a are formed at every predetermined distance, in the central portion in the width direction of the thin elongated sheet 1 having a predetermined width. A plurality of diffusion-limiting membranes 16 are adhered to the bottom surface of the thin elongated sheet 1 to cover the through holes 15. A plurality of positioning holes 13 are formed in the thin elongated sheet 1 in correspondence with every through hole 15, and a plurality of positioning holes 13a are formed in the thin elongated sheet in correspondence with every larger opening 15a. Also, the end detecting holes 14 are formed in the thin elongated sheet 1 in correspondence with the last through hole 15. The thin elongated sheet 1 may be made of a material which has resistance against a test solution. The diffusion-limiting membrane 16 separates interfering particles like blood corpuscle and the like from test solution as its main function, and may consist of polycarbonate membrane having a plurality of minute pores. As a result, when a diffusion-limiting membrane for limiting penetration of the test substance is secured to a concentration measuring electrode 22 which will be described later, the diffusion-limiting membrane 3 prevents a diffusion-limiting membrane secured to the concentration measuring electrode 22 from being clogged. The diffusion-limiting membrane 3 may consist of a membrane to limit penetration of the test substance, and the diffusion-limiting membrane secured to the concentration measuring electrode 22 may be omitted. Employing the diffusion-limiting membrane 3 for separating interfering particles from the target substance as its main function, adhered to the thin elongated sheet 1, and a diffusion-limiting membrane for limiting the penetration of test substance, secured to the surface of the concentration measuring electrode 22, is preferable and prevents reduced accuracy of measurement owing to the interfering particles. It is further preferable that numerals for displaying rest number of the diffusion-limiting membranes 3, are printed on the thin elongated sheet 1 at close position to each through hole 15.

Figure 4:
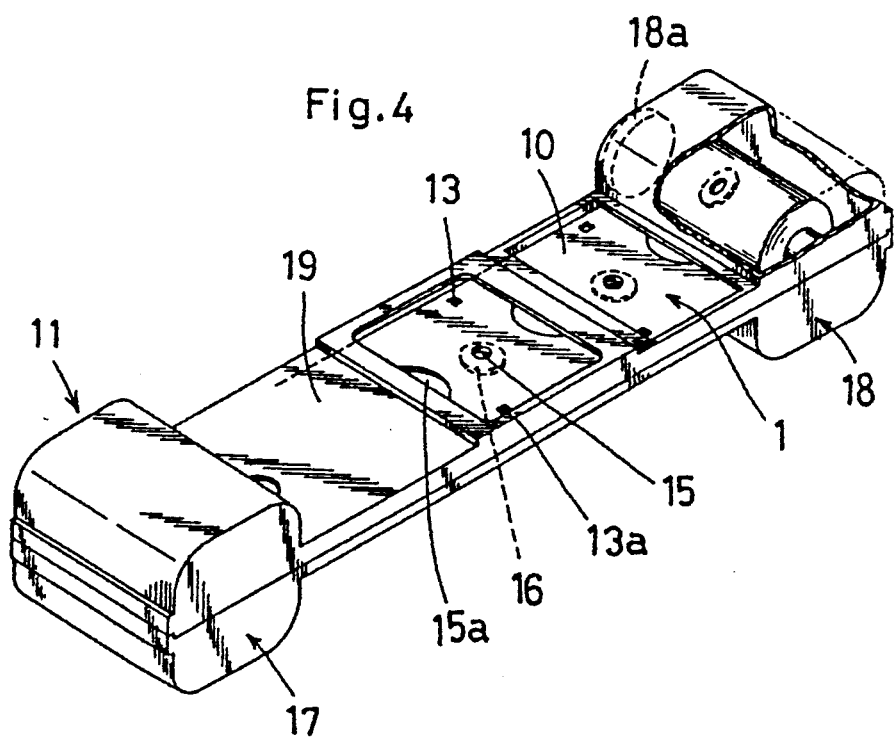
FIG. 4 is a partial cutaway perspective view showing a cartridge in which the diffusion-limiting membrane holding member is housed.
Figure 5:
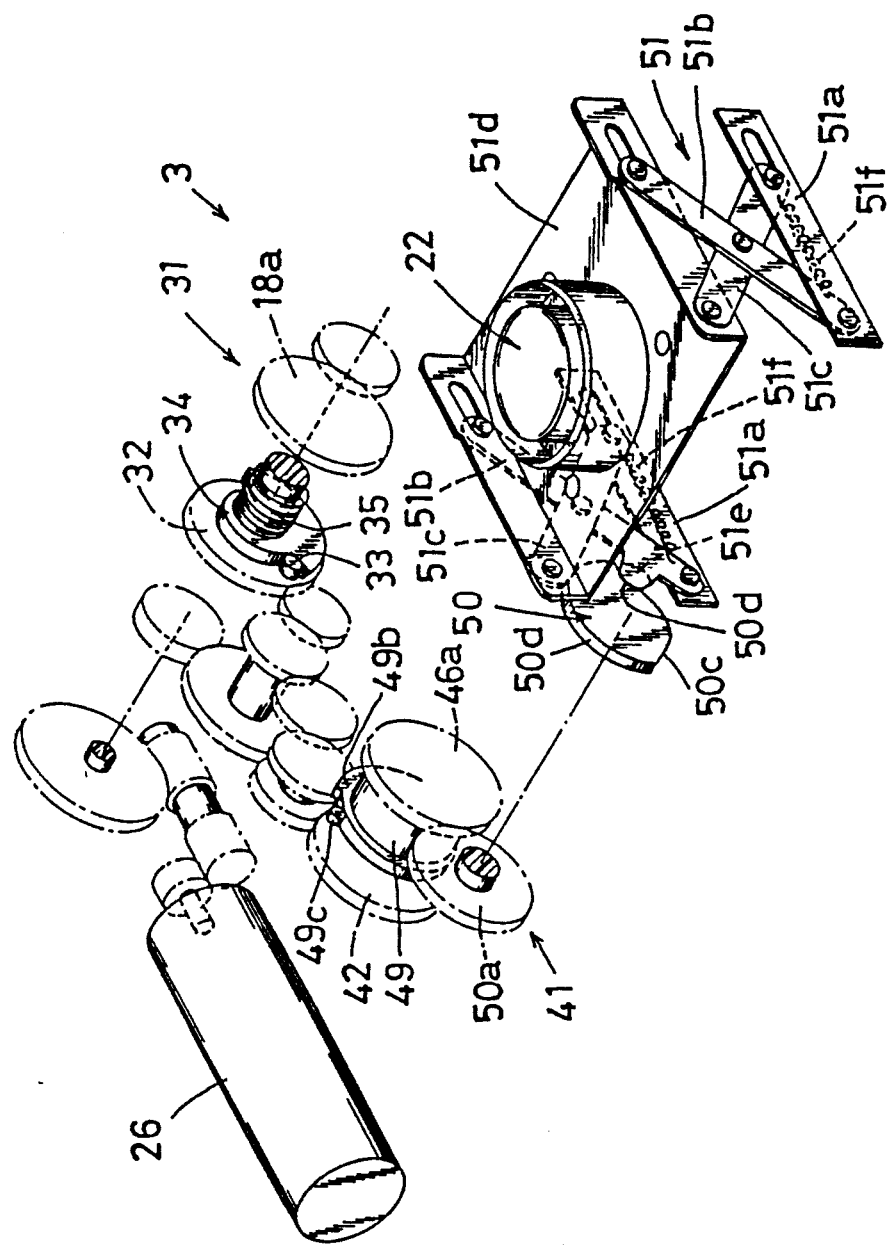
FIG. 5A is a schematic perspective view showing a concentration measuring electrode elevating mechanism.
FIG. 5B is a plan view of the same.
FIGS. 5C and 5D are simplified vertical section views explaining elevation operation of the concentration measuring electrode.
Figure 5B:
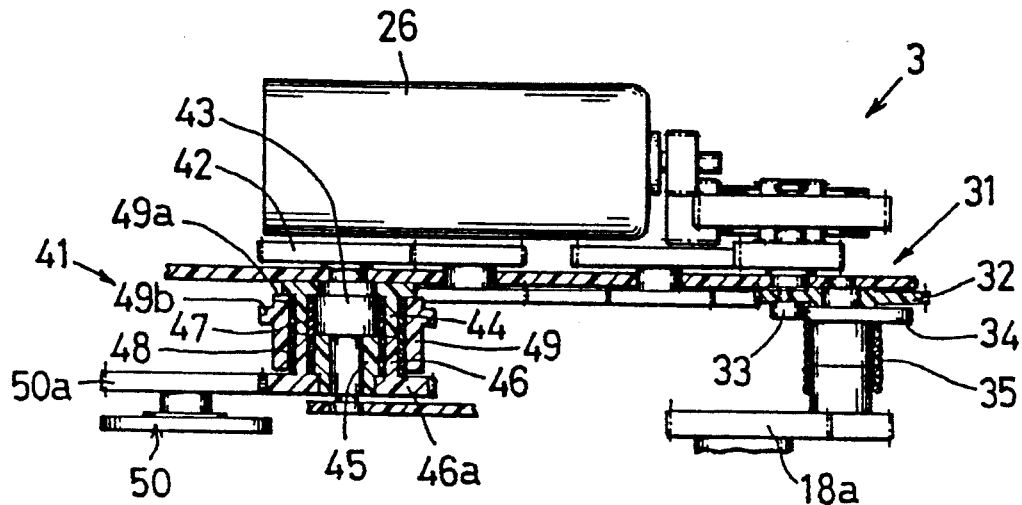
Figure 5C:
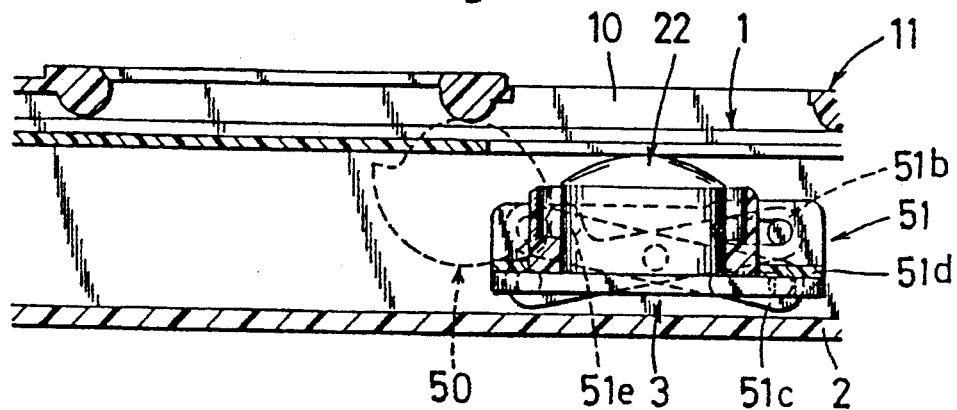
Figure 5D:
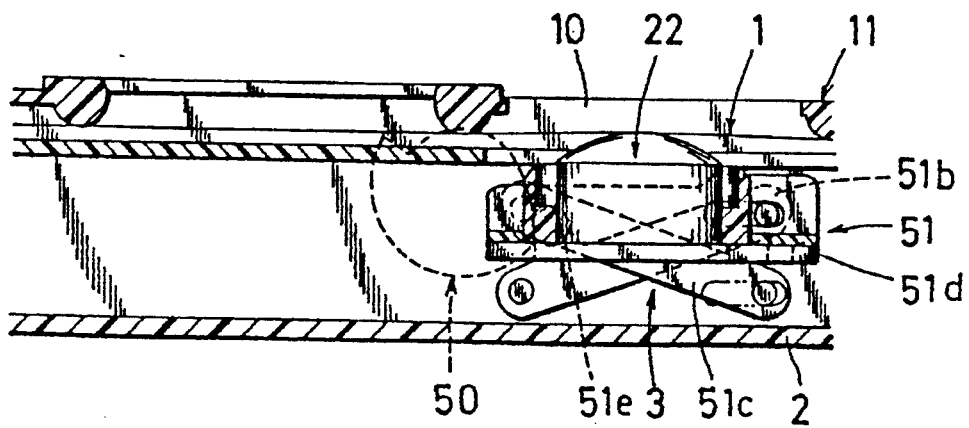

FIG. 4 is a partial cutaway perspective view showing the cartridge housed the thin elongated sheet.

The cartridge 11 has a supplying chamber 17 for housing previously rolled portion of the thin elongated sheet 1, a receiving chamber 18 for receiving and winding the thin elongated sheet 1, and a bridge member 19 for interconnecting the supplying chamber 18 and the receiving chamber 19 in one body. And an opening 10 is formed at the central portion of the bridge member 19. A winding shaft 18a is provided in the supplying chamber 18, and one end of the winding shaft 18a is projected outward from the receiving chamber 18 for receiving rotary force of the motor 26.

The concentration measuring electrode elevating mechanism 3 unites a mechanism for moving the thin elongated sheet 1, as shown in FIGS. 5A to 5D. The mechanism 3 includes two rotary force transmitting mechanisms 31 and 41, each mechanism includes an one-way clutch for performing the elevating operation and the moving operation in synchronism one the other.

The rotary force transmitting mechanism 31 includes a disc 32 rotatable in forward and reverse direction by the motor 26, an engaging pin 33 provided to a predetermined position of the disc 32 and a cam member 34 engaged with the engaging pin 33 and rotated following the disc 32 when the disc 32 is rotated by a predetermined angle. A shaft of the cam member 34 and the winding shaft 18a are disposed coaxially, and an one-way clutch 35 comprising a coil spring wound to transmit the rotary force only in the sheet winding direction, is wound on the shafts.

The construction of the rotary force transmitting mechanism 41 is as follows:

A round rod shaped projection 43 is provided at the center portion of a disc 42 rotatable in forward and reverse direction by the motor 26, and a cylindrical projection 44 coaxial with the projection 43 is provided at the disc 42. A projection 45 having the same diameter with the projection 43 and a cylindrical projection 46 having the same diameter with the cylindrical projection 44 are disposed to opposite to the projection 43 and cylindrical projection respectively, and are connected in one body. One-way clutches 47 and 48 each comprising a coil spring, are provided on the outer surface of both projections 43 and 45 and on the outer surface of both cylindrical projections 44 and 46 respectively. The one-way clutch 47 transmits rotary force in reverse direction of the one-way clutch 48. A regulating cylinder 49 is disposed on the outer surface of the one-way clutch 48. The regulating cylinder 49 has a cutaway portion 49a formed in a predetermined position thereof, to receive one end of a coil spring of the one-way clutch 48 so as to rotate following the one-way clutch 48. The regulating cylinder 49 also has a flange 49b formed on a predetermined extension of the outer surface of the regulating cylinder 49, to release rotary engagement by the one-way clutch 48 when the flange 49b engages with a regulating projection 49c provided at a predetermined position of the test apparatus casing 2. A toothed wheel 46a is provided with the cylindrical projection 46 in one body. A rotary cam member 50 is connected to a toothed wheel 50a geared with the toothed wheel 46a. The rotary cam member 50 includes a small diametered cam portion 50b and a diameter increasing cam portion 50c formed as a part of the rotary cam member 50, the size being determined based on the position of the flange 49b, and also includes a large diametered cam portion 50d formed for the rest extent of the rotary cam member 50 (see FIG. 5A). The rotary force transmitting mechanism 41 further includes a pantograph mechanism 51 for moving the concentration measuring electrode 22 up and down, the pantograph mechanism 51 is driven by the rotary cam member 50. The pantograph mechanism 51 includes a pair of base members 51a being apart by a predetermined distance one the other, two pairs of rods 51b and 51c, a supporting member 51d and an engaging projection 51e. Each rods 51b and 51c are connected at their one end to corresponding base member 51a, and are connected one to the other at their central portion as X-shaped. The supporting member 51d is supported by two pairs of rods 51b and 51c. The engaging projection 51e is provided at a predetermined position of one of the rods 51b so as to engage with the rotary cam member 50. The rods 51b are engaged with the supporting member 51d in a rotatable and slidable manner. The rods 51c are engaged with corresponding base member 51a in a rotatable and slidable manner. Pulling springs are provided between bottom portions of corresponding rods 51b and 51c.

After the thin elongated sheet 1 is housed in the catridge 11 and the catridge 11 is installed in the test apparatus casing 2, concentration measuring operation of test substance in test solution is carried out as follows. With reference to FIG. 6, timing charts showing operation of components, are illustrated.

When necessary operations are not performed at all, both sensors 24 and 25 opposite to the portion of the thin elongated sheet 1 where no positioning holes 13 and 13a and end detecting hole 14 are formed therein, so as to output ON signal from both sensors 24 and 25, thereby the starting portion is detected. In this condition, the concentration measuring electrode 22 contacts an opening of the wetting liquid housing tank 21 through an oval shaped larger opening 15a.

Thereafter, the motor 26 is driven by a control section (not shown) so as to move the concentration measuring electrode 22 downward, then move the thin elongated sheet 1. That is, the motor 26 rotates in a forward direction, rotary force transmitting operation through the one-way clutch 48, until the flange 49a of the regulating cylinder 49 engages with the regulating projection 49c so as to rotate the rotary cam member 50. The concentration measuring electrode 22 is evacuated thereby. When the evacuation of the concentration measuring electrode 22 is finished, the engaging pin 33 engages with the cam member 34. Thereafter, rotary force transmission to the winding shaft 18a through the one-way clutch 35, is carried out so as to move the thin elongated sheet 1. The rotary cam member 50 is kept stopped when the thin elongated sheet 1 is moved, because rotation of the regulating cylinder 49 is prevented.

The moving of the thin elongated sheet 1 by the motor 26 is stopped under the condition that ON signal is outputted from the sensor 24 while OFF signal is outputted from the sensor 25. On this timing, one of the through holes 15 of the thin elongated sheet 1 is opposite to the opening 20 for deposition while one of the larger openings 15a is opposite to the concentration measuring electrode 22. Thereafter, the motor 26 is rotated in reverse direction thereby transmitting rotary force of the motor 26 to the rotary cam member 50 through the one-way clutch 47 so as to elevate the concentration measuring electrode 22.

Afterwards, test solution is dropped onto the through hole 15 positioned on the opening 20, and measuring switch (not shown) is operated for the first time. First, the motor 26 rotates in the forward direction causing the concentration measuring electrode 22 to move downward, then causing the thin elongated sheet 1 to move by a predetermined distance so that the electrode is opposite one of the diffusion-limiting membrane 16. At this time, OFF signal is outputted from the sensor 24 while ON signal is outputted from the sensor 25.

When the test apparatus is able to measure concentration of test substance due to refresh operation of the concentration measuring electrode 22 and the others, the motor 26 is rotated in reverse direction for a short time period causing the concentration measuring electrode 22 to move upward slightly so as to contact with the diffusion-limiting membrane 16. Concentration of the test substance in the test solution is accordingly measured.

After the measurement, the motor 26 is rotated in a forward direction causing the concentration measuring electrode 22 to move downward, then causing the thin elongated sheet 1 to move by a predetermined distance. Thereafter, the motor 26 is rotated in a reverse direction causing the concentration measuring electrode 22 to move upward. At this time, ON signal is outputted again from the sensor 24 while OFF signal is outputted again from the sensor 25.

Concentration of the test substance in the test solution or standard solution can be repeatedly measured by repeating the series of operations above-mentioned.

When the positioning hole 13a and end detecting hole 14 are detected by the sensors 24 and 25 respectively due to the movement of the thin elongated sheet 1, the diffusion-limiting membrane 16 for the next measurement is the last diffusion-limiting membrane. Concentration measuring operations after the additional concentration measuring operation is carried out, are prevented. Display for showing concentration operations with using every diffusion-limiting membrane 16 are done, is made when it is required. An operator can easily recognize the condition through the display. The operator accordingly takes out and throws away the cartridge 11 housing the thin elongated sheet 1 therein. And the operator installs new cartridge 11 housing the thin elongated sheet 1 therein, in the test apparatus casing 2 so as to allow a plurality of concentration measuring operations again.

As is apparent from the foregoing, infection resulting from disease germs is securely prevented from occuring even when the test solution is a body fluid, because the depositing position and concentration measuring positions are apart one from the other.

Second Embodiment

Figure 8:
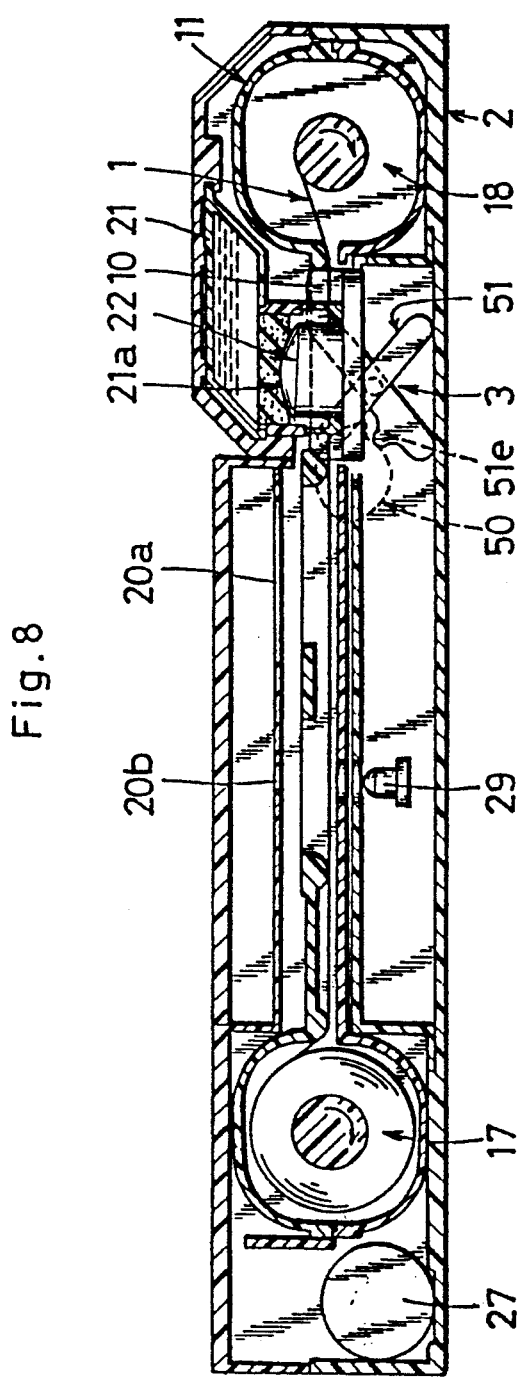
FIG. 8 is a vertical section view of the center portion of the test apparatus in FIG. 7.

FIG. 7 is a partial cutaway perspective view of a test apparatus for measuring concentration of a test substance in liquid in accordance with a second embodiment of the present invention, while FIG. 8 is a vertical section view of the center portion of the test apparatus in FIG. 7.

Differences between the first embodiment and second embodiment are as follows:

(1) Two openings 20a and 20b for deposition are formed disposed in a moving direction of the thin elongated sheet 1.

(2) A motor 27 and rotary force transmitting mechanism (not shown) for transmitting rotary force of the motor 27, are further provided in the test apparatus casing 2.

The distance between both openings 20a and 20b is determined for oppositely locating two through holes 15 of the thin elongated sheet 1 for penetrating test solution, to the openings 20a and 20b simultaneously.

In this embodiment, it is preferable that the deposition of the test solution is carried out through the opening 20a formed at downstream position and deposition of standard solution is carried out through the opening formed at the upstream position. When both openings 20a and 20b are determined as above, the risk of depositing through the wrong opening is avoided even when the depositing is carried out by an inexperienced person.

More specifically, when concentration measuring operations are carried out merely based on test solution, the test solution is deposited onto the diffusion-limiting membrane 16 through the downstream opening 20a. Thereafter, the motor 26 is driven similarly to the first embodiment, causing the thin elongated sheet 1 to move by a necessary and minimum distance, then causing the concentration measuring electrode 22 to contact with the diffusion-limiting membrane 16 so as to perform the concentration measuring operation.

Figure 9:
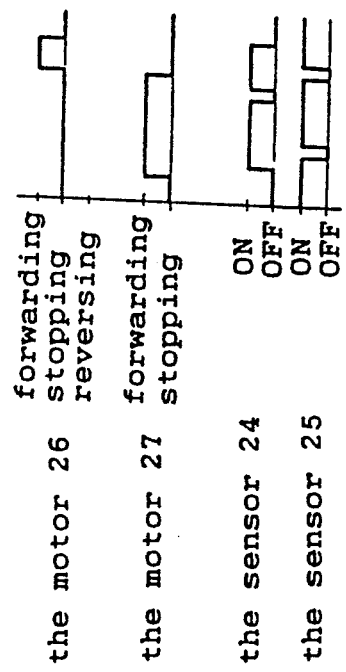
FIGS. 9A and 9B are timing charts explaining concentration measuring operation of the second embodiment.

On the contrary, when the concentration measuring operation is carried out based on a standard solution, the concentration of which is known, prior to the concentration measuring operation based on test solution, for preventing increase of error of measurement with the passage of time, operations are carried out as follows. FIG. 9A is a timing chart showing the concentration measuring operations. First, test solution is deposited onto the diffusion-limiting membrane 16 through the downstream opening 20a, and the standard solution is deposited onto the diffusion-limiting membrane 16 through the upstream opening 20b. Second, the motor 26 is driven similarly to the first embodiment, causing the thin elongated sheet 1 to move by a necessary and minimum distance, then causing the concentration measuring electrode 22 to contact with the diffusion-limiting membrane 16 on which the standard solution is deposited, so as to perform the concentration measuring operation of the standard solution (hereinafter referred to as calibration operation). Thereafter, the thin elongated sheet 1 is moved in the reverse direction by driving the motor 27, then the concentration measuring electrode 22 is contacted with the diffusion-limiting membrane 16 on which test solution is deposited, so as to perform the concentration measuring operation of the test solution. Finally, the thin elongated sheet 1 is moved again by driving the motor 26 so as to locate unused diffusion-limiting membranes 16 opposite to both openings 20a and 20b simultaneously. The next measurement is then able to be carried out.

To raise the positioning accuracy of the thin elongated sheet 1 when the sheet 1 is moved in the reverse direction, the motor 27 is rotated in a forward direction until ON signal is outputted from the sensor 24 and OFF signal is outputted from the sensor 25. This moves the thin elongated sheet 1 in a reverse direction. Then the motor 26 is rotated in a forward direction until OFF signal is outputted from the sensor 24 and ON signal is outputted from the sensor 25 so as to move the sheet 1 in a forward direction. A lowering of the positioning accuracy due to size of positioning hole 13 and the others, is securely avoided.

As is apparent from the foregoing, it is not necessary that depositing position is changed even when the calibration operation and concentration measuring operation are successively carried out in this order, thereby preventing mis-depositing from occurring.

In this embodiment, it is preferable that a lighting device 29 opposite to the upstream side opening 20b for deposition, is further provided. Then light from the lighting device 29 is recognized by an operator through the diffusion-limiting membrane 16 and the through hole 15 thereby greatly increasing the preventing effect of mis-deposition.

Third Embodiment

Figure 11A:
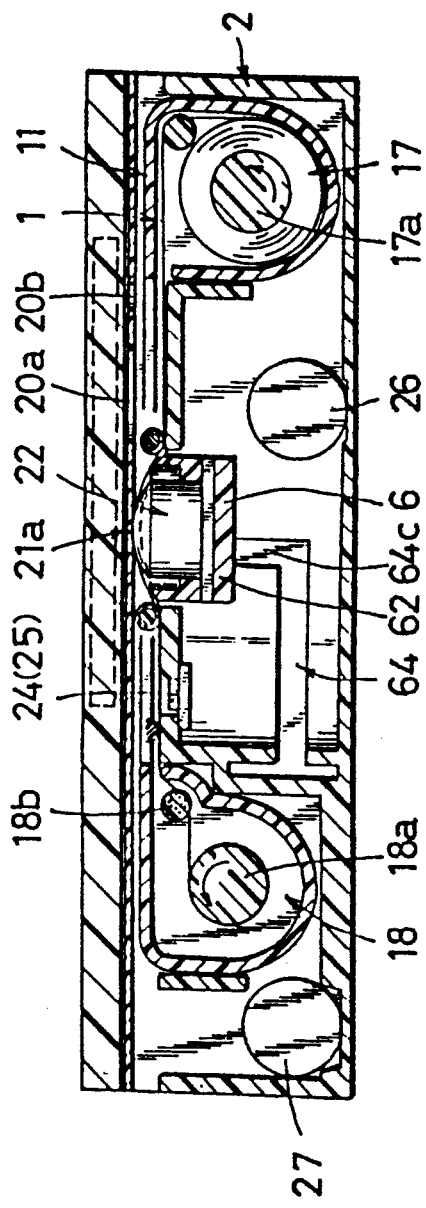
FIGS. 11A and 11B are section views taken along lines XIA—XIA and XIB—XIB in FIG. 10.
Figure 11B:
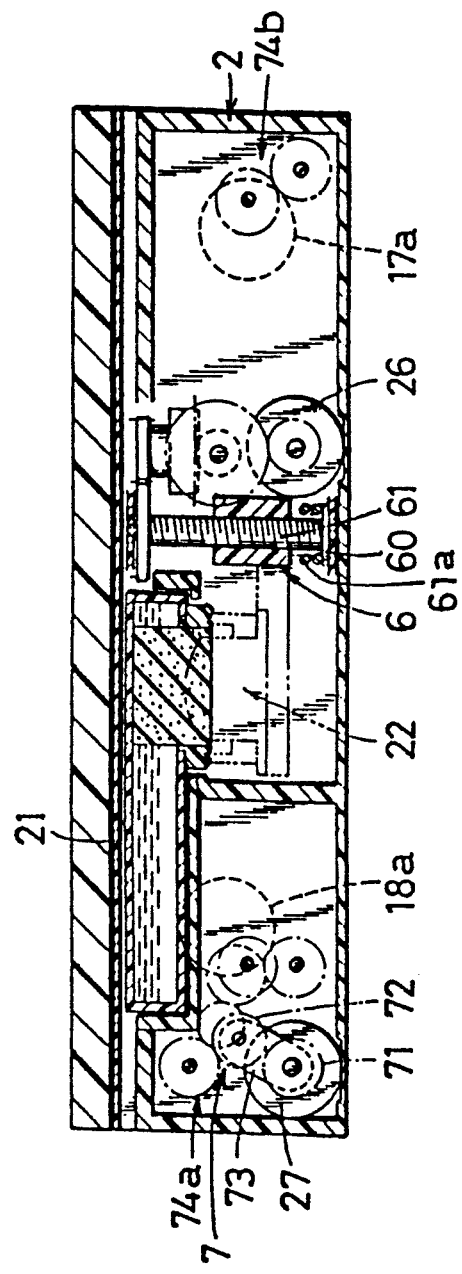

FIG. 10 is a partial cutaway perspective view of a test apparatus for measuring concentration of a test substance in liquid in accordance with a third embodiment of the present invention, while FIGS. 11A and 11B are section views taken along lines XIA—XIA and XIB—XIB in FIG. 10.

The third embodiment differs from the second embodiment as follows:

(1) The wetting liquid housing member 21 is disposed at a position apart from the moving path of the thin elongated sheet 1.

(2) The motor 26 is used only for moving the concentration measuring electrode to and fro.

(3) The motor 27 is used only for moving the thin elongated sheet 1 to and fro.

(4) Only the through holes 15 are formed in the thin elongated sheet 1.

(5) A cleaning member 18b for wiping away test solution and the like, is further provided in the receiving chamber 18 as shown in FIG. 11A.

An electrode driving mechanism 6 for moving the concentration measuring electrode 22 to and fro is illustrated in FIGS. 12A to 12H. The mechanism 6 includes a base member 60 rotatably provided to a predetermined position of the test apparatus casing 2, a screw shaft 61 provided to the base member 60, the screw shaft 61 being moved in forward and reverse direction by the motor 26, a coil spring 61a provided on the screw shaft 61, a support member 62 for supporting the concentration measuring electrode 22, threadedly engaged with the screw shaft 61, a groove 64 for guiding a projection 63 provided to the support member 62 in one body and a regulating mechanism 65 for regulating movement of the projection 63. The groove 64 comprising a horizontal portion 64a extended in a horizontal direction and two vertical portions 64b and 64c, each vertical portion being extended in a vertical direction at the corresponding end of the horizontal portion 64a. At the boundary of the horizontal portion 64a and the vertical portion 64b, the projection 63 is moved selectively along the horizontal portion 64a or the vertical portion 64b only by changing the rotating direction of the screw shaft 61. The regulating mechanism 65 causes the projection 63 to move along the horizontal portion 64a and to move along the vertical portion 64c selectively. The regulating mechanism 65 is rotatable in forward and reverse directions by a predetermined angle around an axis 65a. The angle is determined by two stopper pins 65g secured to the test apparatus casing 2. The mechanism 65 includes a swing member 65c and a stopper arm member 65f. The swing member 65c is energized to rotate in one direction by a spring 65b, and is energized to rotate in reverse direction by the spring 65b when the swing member 65c rotates over a dead point. The stopper arm member 65f is rotatably supported by an axis 65d which is secured to the test apparatus casing 2, by a predetermined angle. The angle is determined by two stopper pins 65h secured to the swing member 65c. And the stopper arm member 65f is energized in one of the rotatable directions selectively by a spring 65e. A part of the stopper arm member 65f is projected into the groove 64. More particularly, the leading edge portion of the stopper arm member 65f is projected into one edge of the horizontal portion 64a or bottom edge vertical portion 64c in correspondence with the energizing direction. And projection length into the groove 64 is determined to be rotated over the dead point by being pressed by the projection 63. The stopper arm member 65f accordingly prevents the projection 63 from moving toward the vertical portion 64b when the projection 63 moves toward the vertical portion 64c along the horizontal portion 64a and presses the swing member 65c. On the contrary, the stopper arm member 65f accordingly prevents the projection 63 from moving upward when the projection 63 moves downward along the vertical portion 64c and presses the swing member 65c. Solenoid plungers and the others may be employed instead of the regulating mechanism 65, to perform the similar operation.

A sheet driving mechanism 7 for moving the thin elongate sheet 1 to and fro by the motor 27 is schematically illustrated in FIG. 13.

The mechanism 7 includes a driving pinion 71 secured to a rotary shaft of the motor 27, a toothed wheel 72 threadedly engaged with the driving pinion 71 and a support member 73 for supporting the toothed wheel 72 rotatably, the support member 73 being rotatable around the rotary shaft of the motor 27. A first transmitting mechanism 74a is provided for transmitting rotary force to the thin elongate sheet in a forward direction and a second transmitting mechanism 74b is provided for transmitting rotary force to the thin elongate sheet in backward direction, each transmitting mechanism threadedly engage with the toothed wheel 72 selectively when the support member 73 rotates to the limit. The toothed wheel 72 accordingly rotates in the same direction of the rotary shaft of the motor 27, and threadedly engages with the corresponding transmitting mechanism. As a result, forward and backward movement of the thin elongate sheet 1 is easily selected by only selecting rotary direction of the motor 27. In FIG. 13, a supplying shaft 17a and a receiving shaft 18a are illustrated.

Operations of the test apparatus having the arrangement above-mentioned, are as follows.

(1) Case 1 (illustrated in FIG. 14A)

This case describes operations for measuring concentration based on a test solution only.

The motor 27 is interlocked in its rotation in its reverse direction with an opening operation of a cover (not shown) of the test apparatus casing 2 so as to move the thin elongated sheet 1 in a backward direction until two of the through holes 15 are positioned opposite to the openings 20a and 20b. In this state, the test solution is deposited onto one of the through holes 15 through the downstream side opening 20a for deposition, then the motor 27 is rotated in a forward direction so as to move the thin elongated sheet 1 by a predetermined distance in a forward direction. In this state, OFF signal is outputted from the sensor 24 due to opposite location of the positioning hole 13 to the sensor 24 while ON signal is outputted from the sensor 25. Thereafter, the concentration measuring electrode 22 is apart from the wetting liquid housing tank 21 and is further moved downward, then is moved in horizontal direction, and then is moved upward. The movement of the concentration measuring electrode 22 is performed by rotating the motor 26 in forward direction. And at the end of the upward movement, the concentration measuring electrode 22 contacts with the diffusion-limiting membrane 16 and measuring of concentration of test solution is performed. Finally, the concentration measuring electrode 22 is moved backward so as to contact with the wetting liquid housing tank 21 by rotating the motor 26 in reverse direction, then the thin elongated sheet 1 is moved forward by twice the distance between neighboring through holes 15 by rotating the motor 27 in forward direction. Then, the next measurement is able to be carried out.

The operations of the regulating mechanism 65 following movement of the concentration measuring electrode 22, are as follows and illustrated in FIGS. 12B to 12H. The description is made for only backward movement of the concentration measuring electrode 22.

Figure 12A:
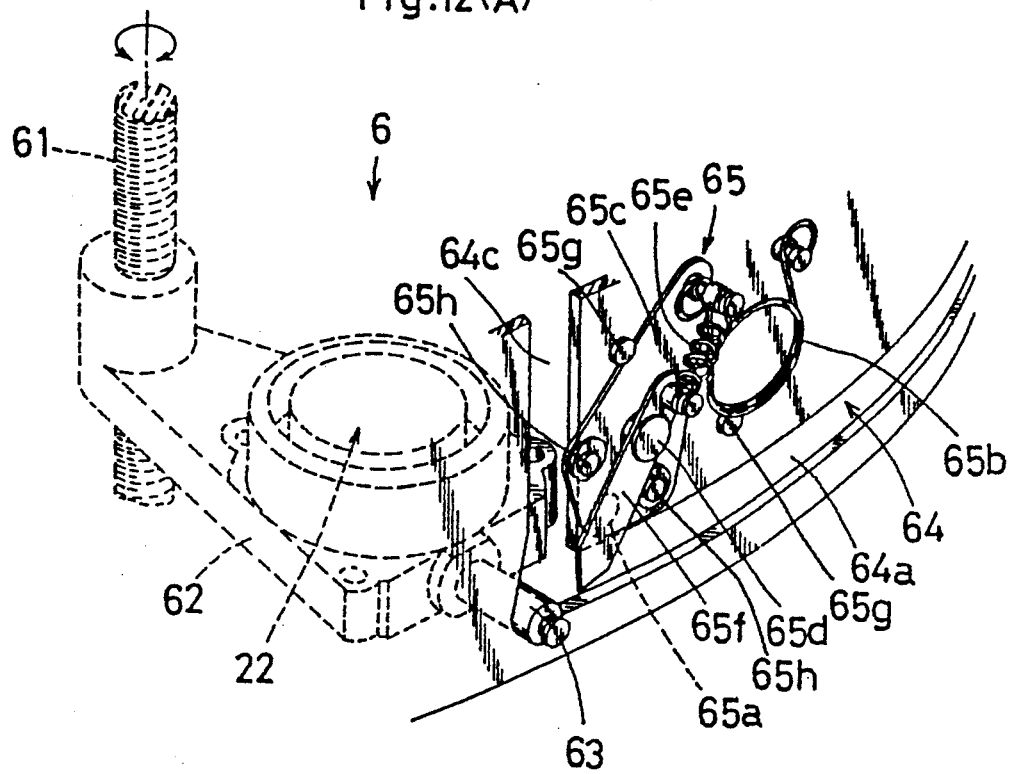
FIG. 12A is a schematic perspective view showing a concentration measuring electrode driving mechanism.
Figure 12B:
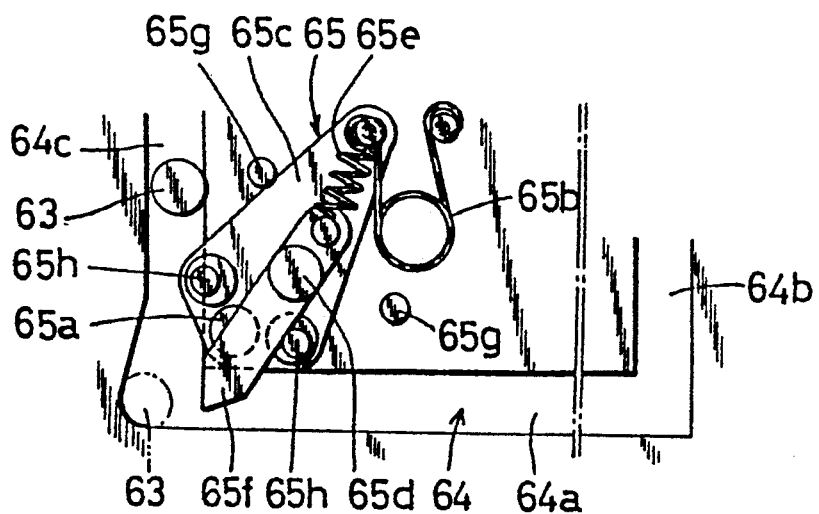
FIGS. 12B to 12G are diagrams useful in understanding the operation of the concentration measuring electrode driving mechanism.
Figure 12C:
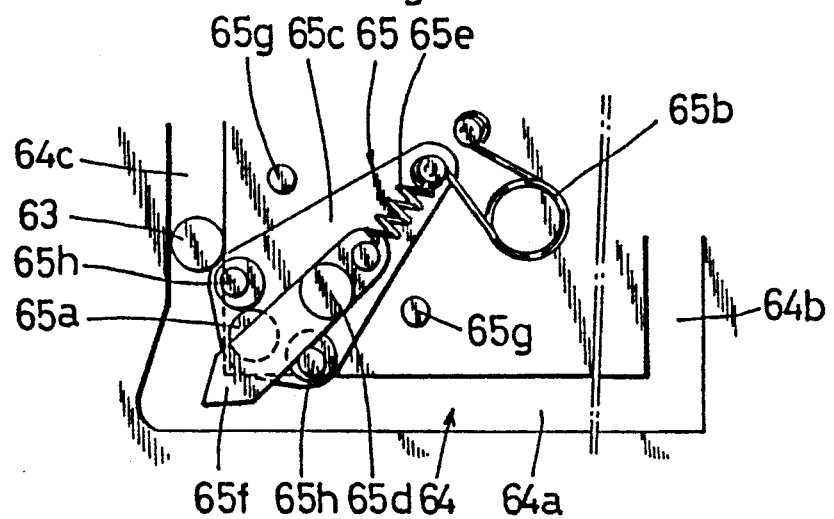
Figure 12D:
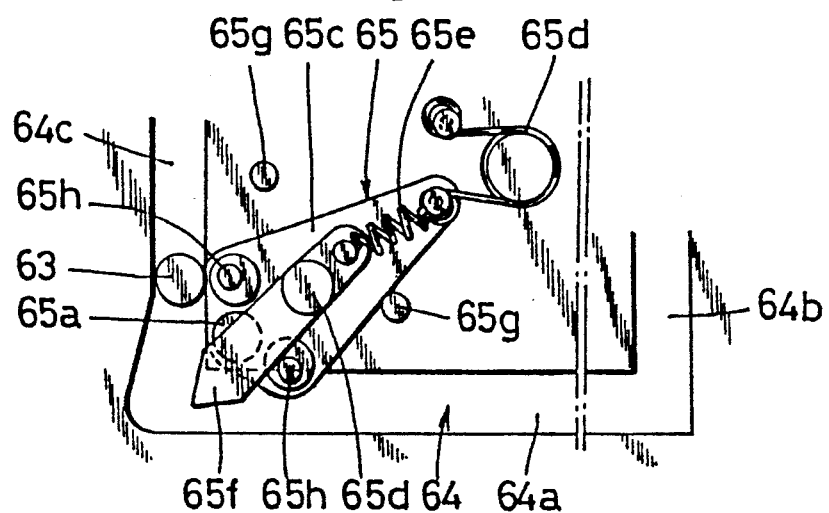
Figure 12E:
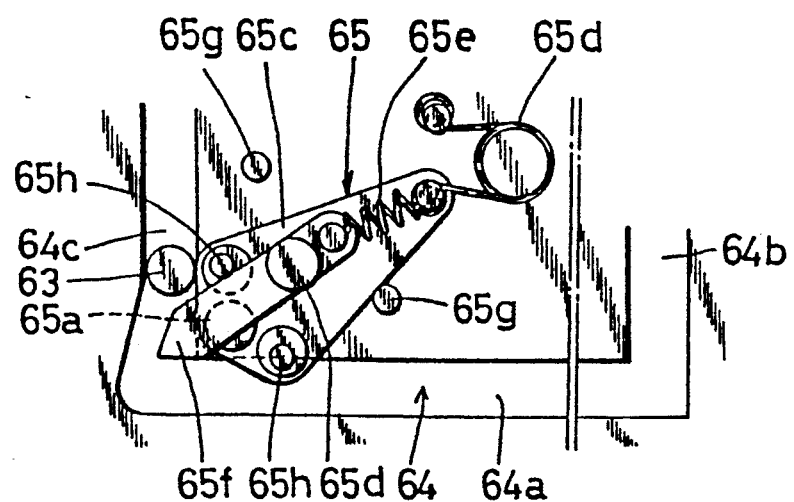
Figure 12F:
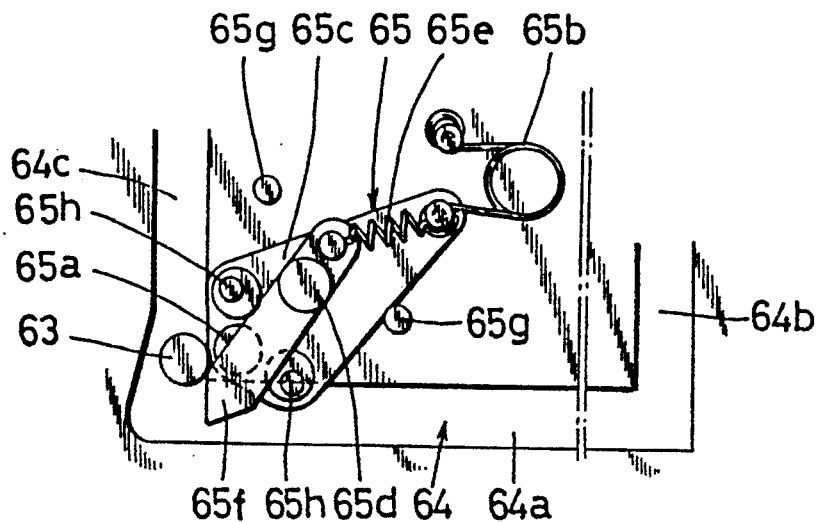
Figure 12G:
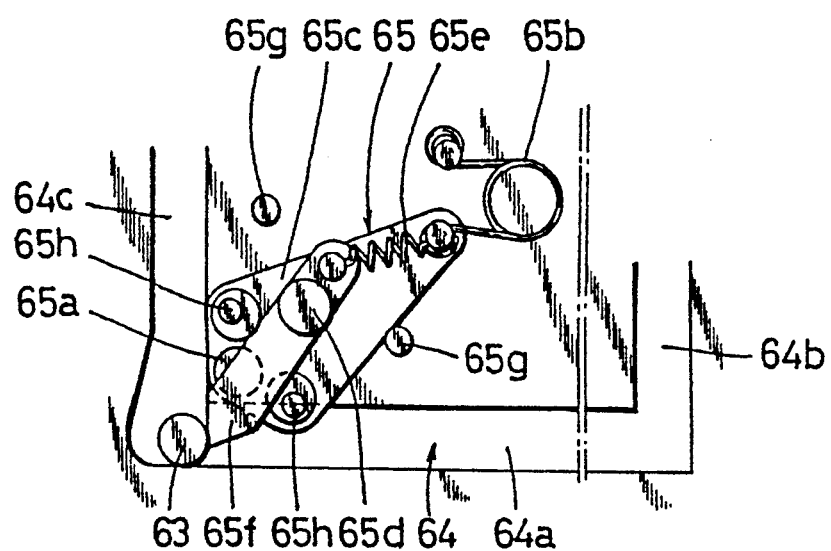
Figure 12H:
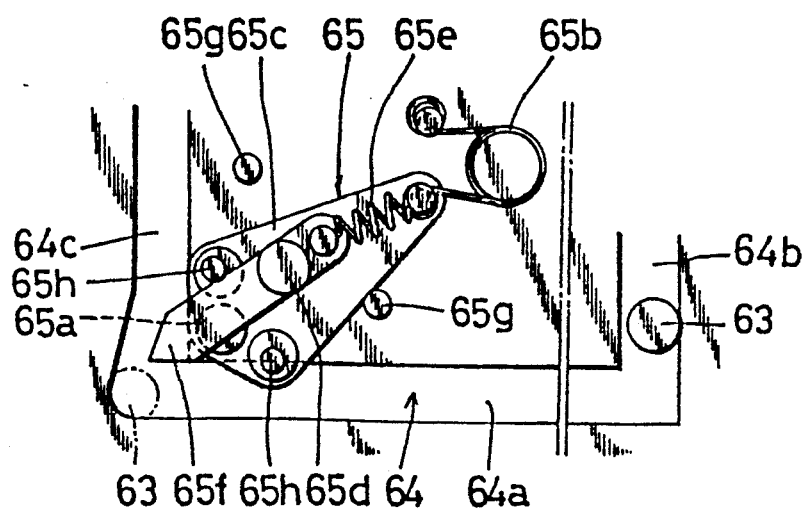

First, the projection 63 moves downward as illustrated in FIG. 12B, then the swing member 65c is rotated in a clockwise direction around the axis 65a by being pressed by the projection 63 as illustrated in FIG. 12C. The swing member 65c is further rotated by being further pressed due to further movement of the projection 63 so as to rotate over the dead point causing the spring 65b to be quickly turned as illustrated in FIG. 12D. The spring 65b accordingly applies energizing force in the reverse direction to the swing member 65c. Then the stopper arm member 65f is turned in a clockwise direction by the spring 65e as illustrated in FIG. 12E. The projection 63 further moves in a downward direction so as to contact and rotate the stopper arm member 65f in a counter clockwise direction as illustrated in FIGS. 12F and 12G. After the projection 63 moves to the bottom of the vertical portion 64c as illustrated in FIG. 12G, the projection 63 moves horizontally a little bit apart from the stopper arm member 65f as illustrated by dot-dash line in FIG. 12H so as to rotate the stopper arm member 65f in a clockwise direction as illustrated in FIG. 12H. Thereafter, the projection 63 can be moved along the horizontal portion 64a and vertical portion 64b successively. When the projection 63 is moved along the horizontal portion 64a, the support member 62 is lowered so as to pressure contact with the coil spring 61a thereby the support member 62 is securely rotated following the rotation of the screw shaft 61, due to the friction between the coil spring 61a and the support member 62.

Concentration of test substance in test solution can be repeatedly measured by repeating the series of operations above-mentioned, without installing and disposing of the diffusion-limiting membrane 16.

As is apparent from the foregoing, infection resulting from disease germs is securely prevented from occuring even when test solution is body fluid, because the concentration measuring electrode 22 contacts with the wetting liquid housing tank 21 instead of being opposite to the opening 20a for deposition. Additionally, test solution is wiped away just after each concentration measuring operation is finished.

In this embodiment, it is possible that the operation for moving the thin elongated sheet 1 in a backward direction prior to deposition, and the operation for moving the thin elongated sheet 1 in a forward direction after the measurement, are omitted.

Figure 14B:
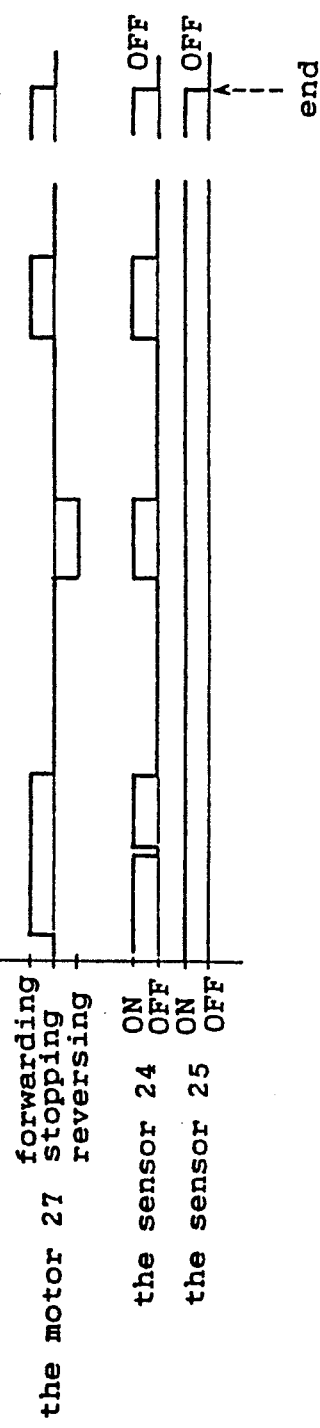
Figure 14C:
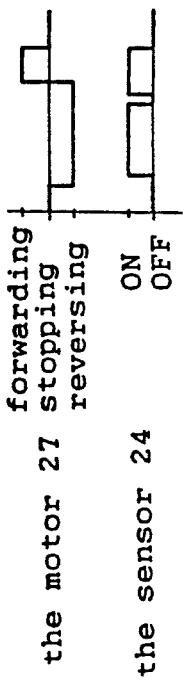

(2) Case 2 (illustrated in FIG. 14B)

This case describes operations for calibration based on standard solution for calibration and operations for measuring concentration based on test solution. The operations for calibration are carried out prior to operations for measuring concentration.

Standard solution is deposited to a through hole 15 through the upstream side opening 20b while test solution is deposited to a through hole 15 through the downstream side opening 20a. Then the thin elongated sheet 1 is moved by a predetermined distance by driving the motor 27. In this state, the diffusion-limiting membrane 16 covering the through hole 15 having deposited standard solution thereon, is able to contact with the concentration measuring electrode 22, because the distance is determined to be twice the distance between neighboring through holes 15. Thereafter, the concentration measuring electrode 22 is moved in a downward direction so as to be apart from the wetting liquid housing tank 21, then is moved in horizontal direction and in upward direction successively by driving the motor 26. At the end of movement in upward direction, the concentration measuring electrode 22 is contacted with the diffusion-limiting membrane 16, then concentration measurement of standard solution is carried out and the calibration operation is carried out based on result of measurement.

Thereafter, the concentration measuring electrode 22 is moved apart from the diffusion-limiting membrane 16 by driving the motor 26 in reverse direction, then the thin elongated sheet 1 is moved in a backward direction by the distance between neighboring through holes 15 by driving the motor 27 in reverse direction, afterwards, the concentration measuring electrode 22 is contacted with neighboring diffusion-limiting membrane 16 so as to perform the concentration measuring operation based on the test solution. Finally, the concentration measuring electrode 22 is moved in the reverse direction by driving the motor 26 in reverse direction so as to contact the concentration measuring electrode 22 with the wetting liquid housing tank 21, then the thin elongated sheet 1 is moved in a forward direction corresponding to the distance between neighboring through holes 15 by driving the motor 27 in the forward direction. Then next measurement is able to be carried out.

Concentrations of test substance in standard solution and in test solution can be repeatedly carried out by repeating the series of operations above-mentioned, without installing and disposing of the diffusion-limiting membrane 16.

In this embodiment, it is preferable that first, the thin elongated sheet 1 is moved forward so as to perform calibration operation, second, the thin elongated sheet 1 is moved backward so as to perform concentration measurement based on the test solution, and third, the thin elongated sheet 1 is moved forward by twice the distance between neighbouring through holes 15. Standard solution and test solution are accordingly wiped away just after each calibrating operation and the concentration measuring operation are finished.

To increase positioning accuracy of the thin elongated sheet 1 when it is moved backward, first, the thin elongated sheet 1 is moved backward by rotating the motor 27 in the reverse direction until ON signal is outputted from the sensor 24, second, the thin elongated sheet 1 is moved forward by rotating the motor 27 in the forward direction until OFF signal is outputted from the sensor 24. As a result, a decrease in the positioning accuracy due to size of the positioning hole 13 and the others, is securely avoided.

Figure 15:
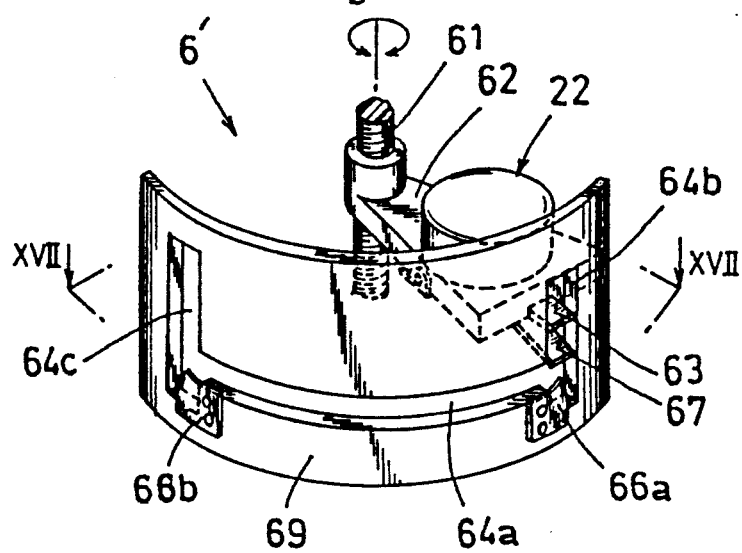
FIG. 15 is a perspective view of an electrode driving mechanism having different arrangement from the concentration measuring electrode driving mechanism in FIG. 12A.

FIG. 15 is a perspective view of an electrode driving mechanism 6' having a different arrangement from the electrode driving mechanism 6.

Differences in the electrode driving mechanism 6' are as follows.

(1) Vertical portions 64b and 64c are extended so as to position their bottom below the horizontal portion 64a.

(2) Two plate springs 66a and 66b are provided to a curved plate member 69 of the test apparatus casing 2 instead of the regulating mechanism 65.

Figure 16:
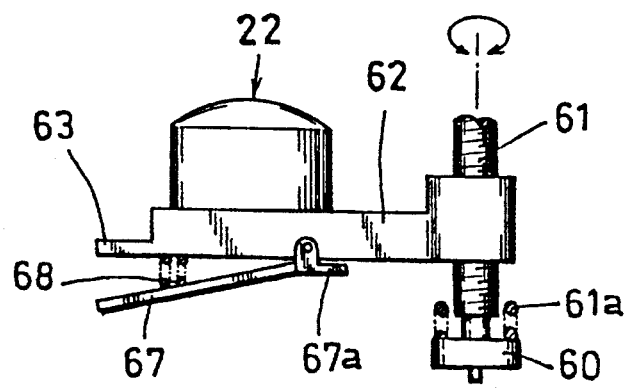
FIG. 16 is a side view of a main portion in FIG. 15.

(3) A swing arm member 67 is provided to the support member 62 as is illustrated in FIG. 16.

(4) A spring 68 for energizing the swing arm member 67 downward, is provided to the support member 62 as is illustrated in FIG. 16.

Figure 17:
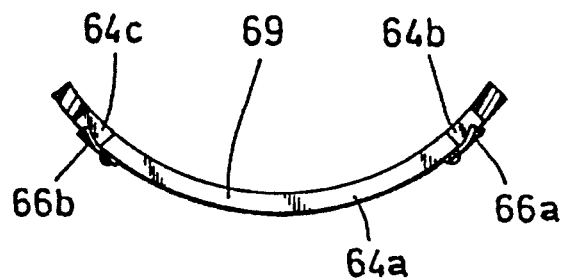
FIG. 17 is a section view taken along lines XVII—XVII in FIG. 15.

Each plate spring 66a is secured to a curved plate member 69 in its base portion and is extended in a corresponding vertical portion in its upper part of leading edge portion as is illustrated in FIG. 17. Lower part of the leading edge portion is laying along the outer surface of the curved plate member 69. An upper edge of the plate spring 66a is extended so as to be opposite to the bottomward portion of the horizontal portion 64a.

The upper edge of the leading edge portion of the plate spring 66a is most protruded in its corresponding vertical portion while the lower edge is not protruded at all.

The swing arm member 67 has a regulating member 67a for limiting its downward movement, as is illustrated in FIG. 16.

Operation of the electrode driving mechanism 6' is as follows.

Figure 18A:
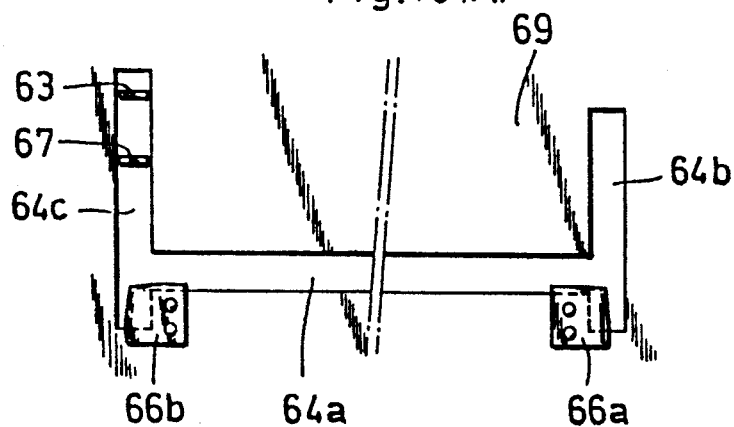
FIGS. 18A to 18F are diagrams useful in understanding the operation of the electrode driving mechanism.

When the concentration measuring electrode 22 contacts with the wetting liquid housing tank 21, the projection 63 is at the top position of the vertical portion 64c while the swing arm member 67 is located at a downward limit position from the projection 63, as is illustrated in FIG. 18A. In this state, the support member 62 is located apart from the coil spring 61a so as not to transmit the force to the support member 62 for rotating the support member 62 following the screw shaft 61. As a result, the support member 62 is moved upward and downward smoothly by rotating the screw shaft 61.

Figure 18B:
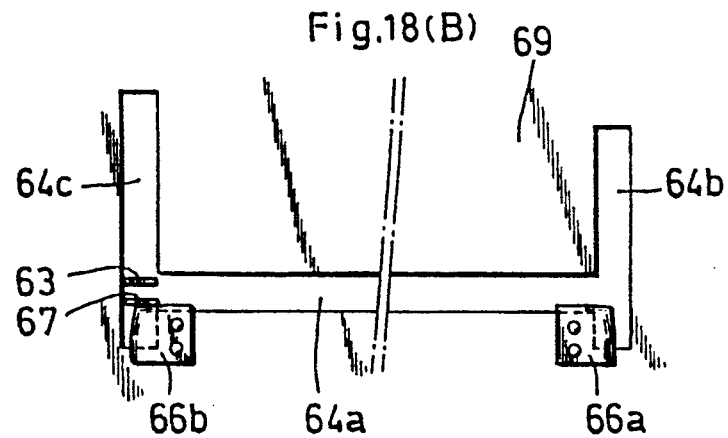

Thereafter, the projection 63 is moved downward by rotating the screw shaft 61, and the swing arm member 67 is then contacted with the upper edge of the plate spring 66b. The projection 63 is further moved downward so as to press the spring 68, and is close to the swing arm member 67, as is illustrated in FIG. 18B. The height from the bottom of the swing arm member 67 to the top of the projection 63 is smaller than the height of the horizontal portion 64a. And the support member 62 is close to the base member 60 resulting the coil spring 61a pressed, so as to generate enough friction therebetween.

Figure 18C:
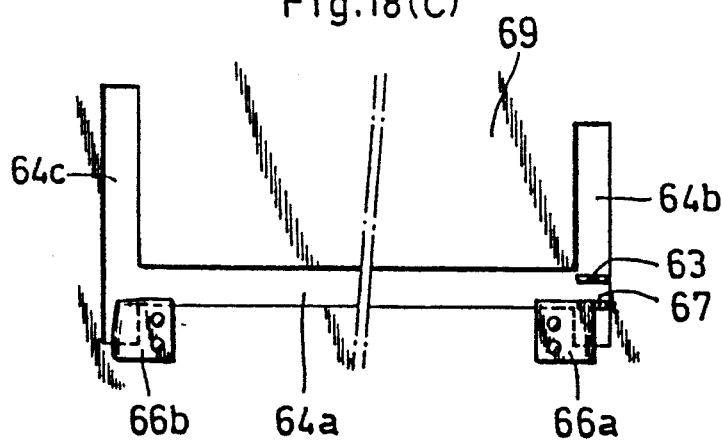
Figure 18D:
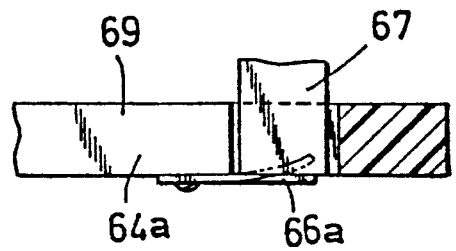
Figure 18E:
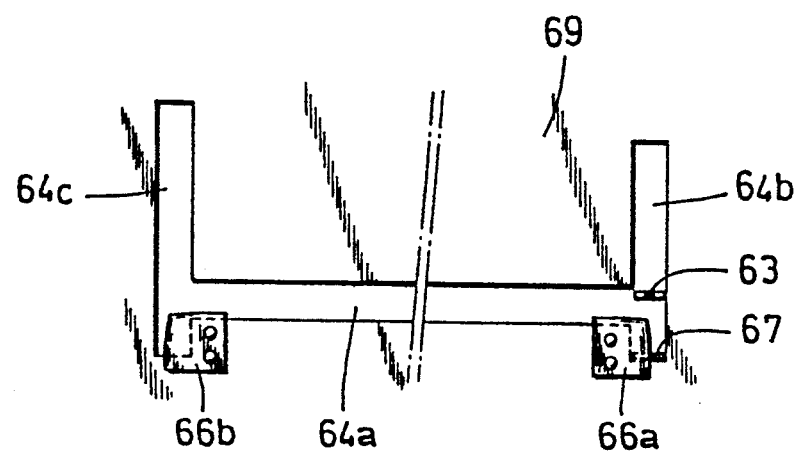
Figure 18F:
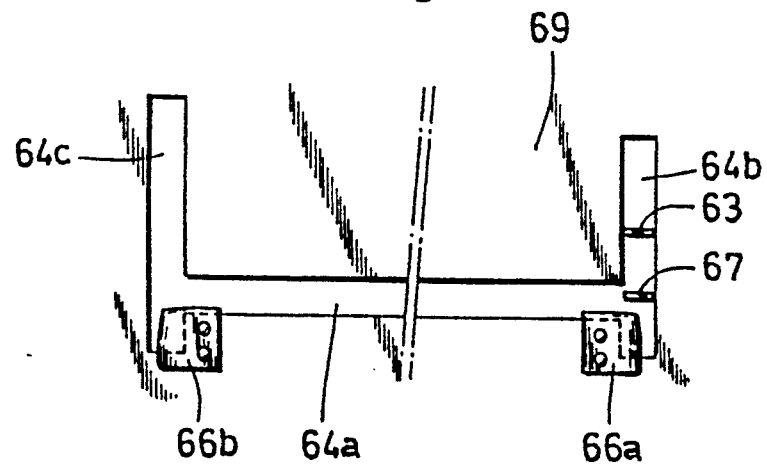

Then the support member 62 rotates following the rotation of the screw shaft 61 due to friction between the support member 62 and the spring 61a, and the swing arm member 67 disengages with the plate spring 66b and then engages with the bottom of the horizontal portion, at early stage of the rotation of the support member 62. At end of the rotation of the support member 62, leading edge of the swing arm member 67 engages inner surface of upper portion of the plate spring 66a so as to deform the plate spring 66a as is illustrated in FIGS. 18c and 18d. And the swing arm member 67 swings downward by the spring 68 due to disengagement of the swing arm member 67 and the horizontal portion 64a, as is illustrated in FIG. 18E, because the pressing force of the plate spring 66a to the swing arm member 67 decreases following descending of pressing portion of the plate spring 66a. Thereafter, the projection 63 and the swing arm member 67 moves upward with keeping the projection 63 and the swing arm member 67 being apart one from the other, by rotating the screw shaft 61, as is illustrated in FIG. 18F. The support member 62 elevates smoothly following the rotation of the screw shaft 61, because the pressing force of the support member 62 to the coil spring 61a decreases when the support member 62 elevates a little distance so as to decrease the friction therebetween and the rotary force transmitted to the support member 62 following the rotary of the screw shaft 61, is decreased accordingly. During the upward movement of the projection 63, the projection 63 and the swing arm member 67 does not locate opposite to the horizontal member 64a simultaneously. As a result, the horizontal movement of the support member 62 is securely prevented.

When the concentration measuring electrode 22 moves in the reverse direction, operations similar to the above-mentioned operations are performed.

The length of the coil spring 61a is preferably determined to be short so as not to apply the spring force to the support member 62 until the support member 62 is descended sufficiently, and to descend smoothly the support member 62 following the rotation of the screw shaft 61. The spring force of the coil spring 61a is determined to be strong so as to generate enough friction due to pressing of the coil spring 61a by the support member 62 which is descended sufficiently, and to rotate smoothly the support member 62 following the rotation of the screw shaft 61. The spring force of the coil spring 61a is preferably determined not to be great so as not to increase the rotary force of the screw shaft 61.

In this embodiment, it is preferable that a lighting device (not shown) is provided opposite to the upstream side opening 20b for deposition. Then light from the lighting device is passed through the diffusion-limiting membrane 16 and the through hole 15 thereby increasing the prevention effect against mis-deposition.

Fourth Embodiment

Figure 19:
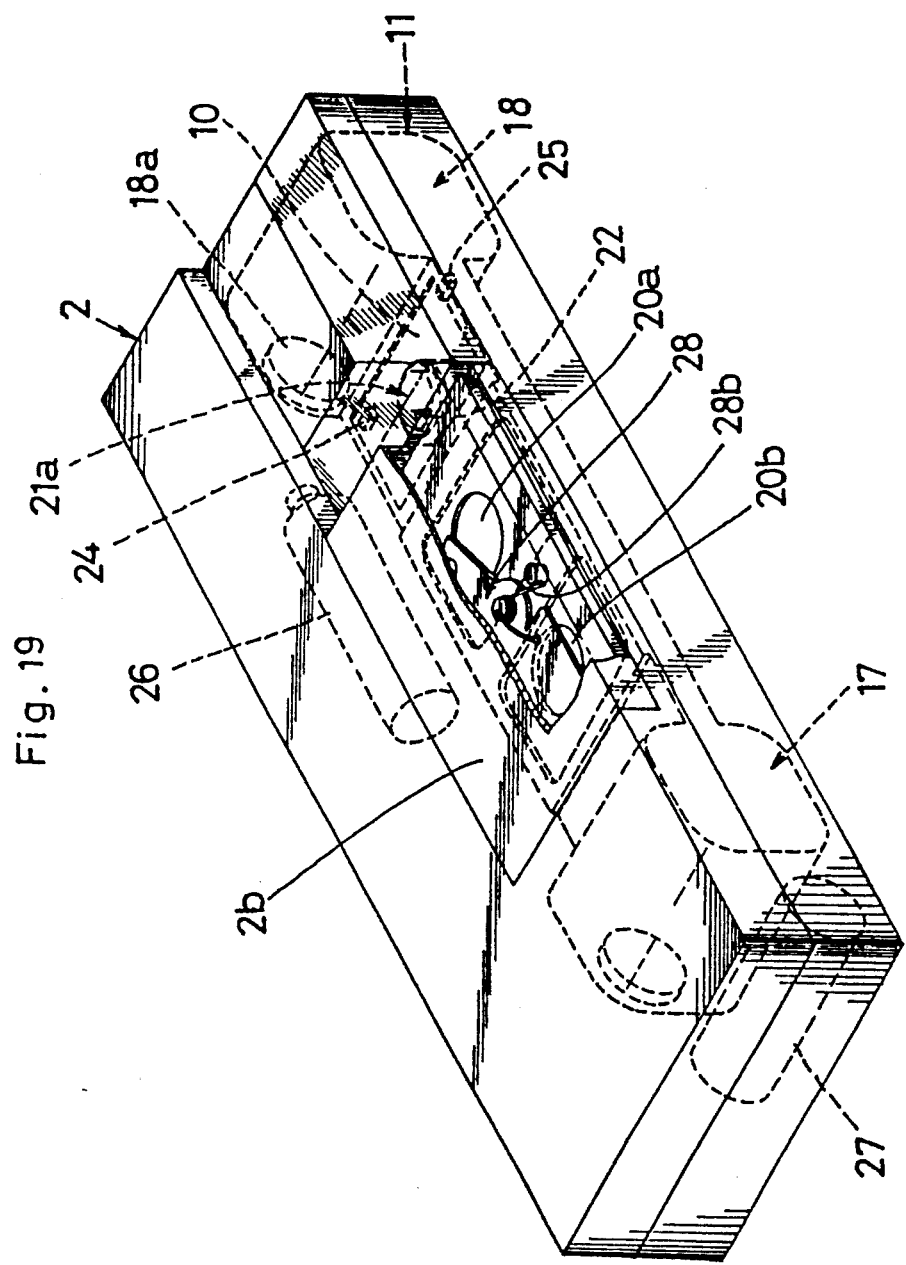
FIG. 19 is a partial cutaway perspective view of a test apparatus for measuring concentration of a test substance in liquid in accordance with a fourth embodiment of the present invention.

FIG. 19 is a schematic perspective view of a test apparatus for measuring concentration of a test substance in liquid in accordance with a fourth embodiment of the present invention.

The fourth embodiment differs from the second embodiment in that a cover member 28 is provided for selectively covering one of the pair of openings 20a and 20b for deposition, to the test apparatus casing 2.

The cover member 28 is interlocked in its rotation with an opening operation of a cover 2b of the test apparatus casing 2. Which opening is to be covered is determined by operating measuring mode selection switch or the like (not shown) provided to the test apparatus casing 2. And a smaller opening 28a for depositing standard solution is provided in a predetermined position for covering the downward opening 20a, of the cover 28. It is preferable that whether or not calibration is needed to be carried out, is detected based on the condition of the concentration measuring electrode 22, or is determined by manual operation so as to rotate the cover member 28 following opening operation of the cover 2b in correspondence with the detection or the determination.

Figure 20A:
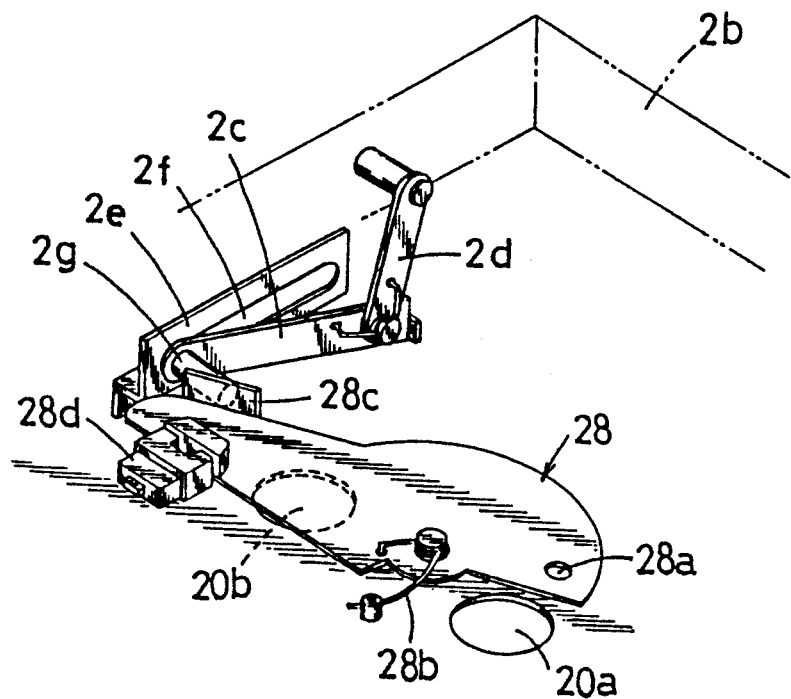
FIGS. 20A to 20C are diagrams useful in understanding the operation of a cover.
Figure 20B:
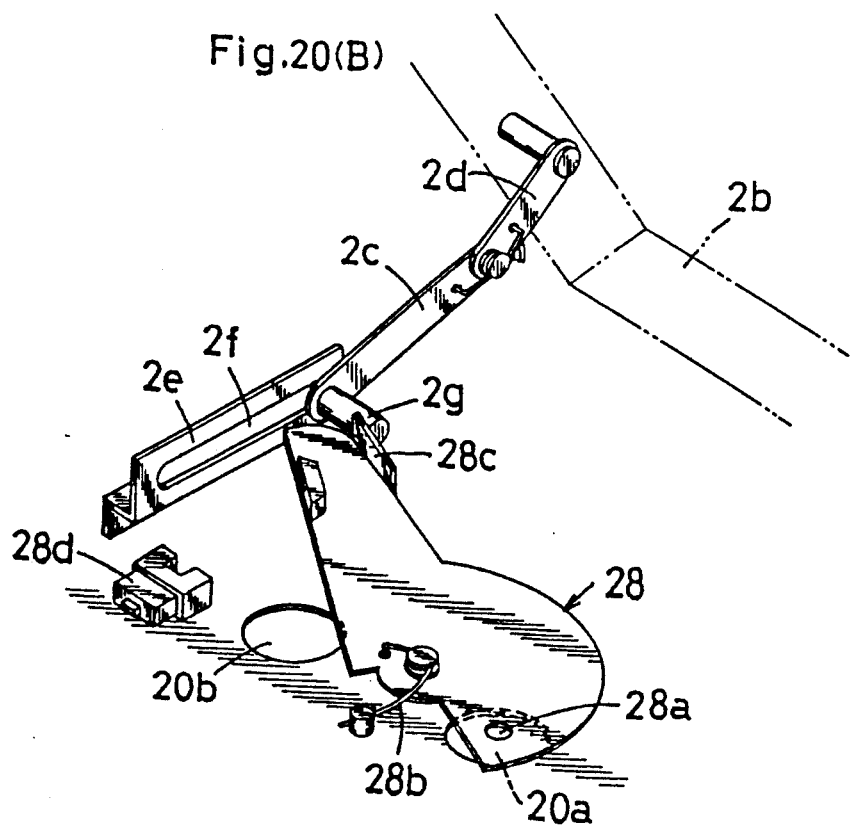
Figure 20C:
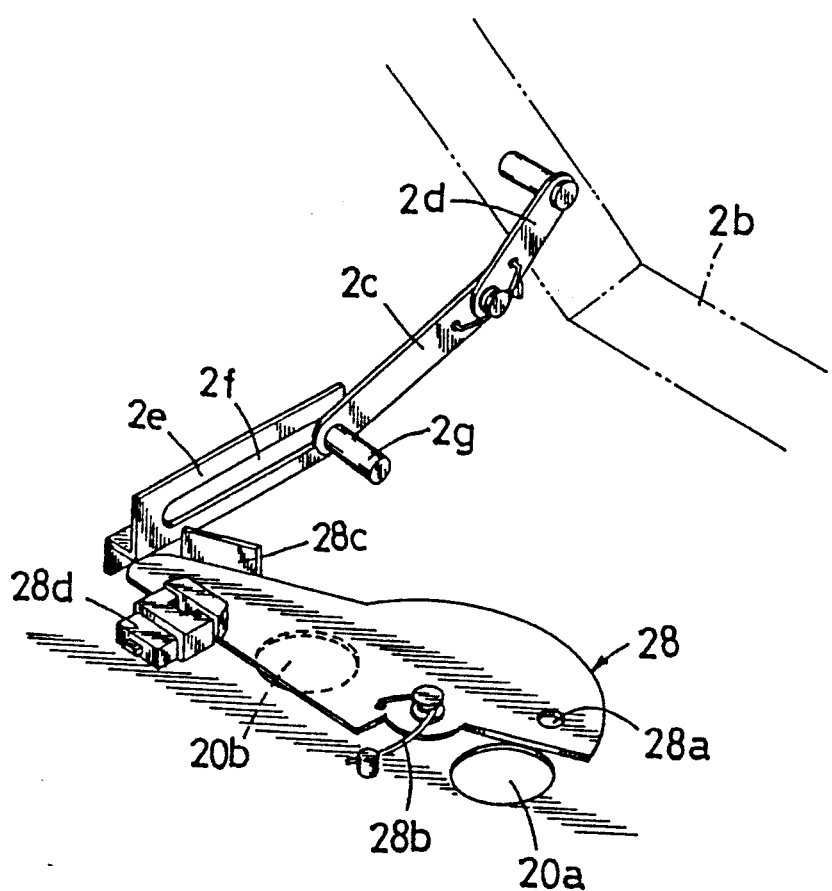

A cover member driving mechanism is illustrated in FIGS. 20A to 20C.

The mechanism includes a first arm member 2c rotatably provided to a predetermined position of the cover 2b by laying a second arm member 2d therebetween, a guiding member 2e having an elongated opening 2f for regulating movement of the leading edge portion of the first arm member 2c, a regulating pin 2g for regulating rotation of the cover member 28 provided to the leading edge portion of the first arm member 2c, a spring 28b for energizing the cover member 28 to be rotated towards the regulating pin 2g, an engaging member 28c for engaging with the regulating pin 2g, provided to a predetermined position of the cover member 28 and a repulsion-type solenoid 28d for attracting and holding the cover member 28, provided to a predetermined position of the test apparatus casing 2.

When the concentration measuring operation is based on only a test solution, supplying power to the solenoid 28d is stopped so as to keep the attraction and holding of the cover member 28 against the spring 28b by the solenoid 28d thereby keeping the cover member 28 in its rotated state to cover the upstream side opening 20b, as is illustrated in FIGS. 20A and 20C. A through hole 15 is accordingly revealed through only the downstream side opening 20a. Concentration measuring operation is carried out by depositing test solution to the open through hole 15, and then by moving the thin elongated sheet 1 and moving the concentration measuring electrode 22.

When calibration operation is carried out prior to concentration measuring operation based on test solution, power is supplied to the solenoid 28d so as to rotate the cover member 28 by the spring 28b, as is illustrated in FIG. 20B. A through hole 15 is accordingly open through only the upstream side opening 20b, and another through hole 15 is slightly open through the downstream side opening 20a and the smaller opening 28a. Test solution is deposited to the through hole 15 open through the opening 20b while standard solution is deposited to the through hole 15 revealed through the opening 20a and the smaller opening 28a. Thereafter, calibration operation and concentration measuring operation based on test solution are successively carried out by performing moving operation of the thin elongated sheet 1 and moving of the concentration measuring electrode 22 twice.

As is apparent from the foregoing, mis-deposition is securely prevented from occuring in this embodiment because only the through hole 15 permitting the deposition of test solution is sufficiently open.

It is preferable that a cover member driving mechanism for rotating the cover member 28 simply by a solenoid or the like may be employed instead of the cover member driving mechanism having the arrangement above-mentioned.

Fifth Embodiment

Figure 21:
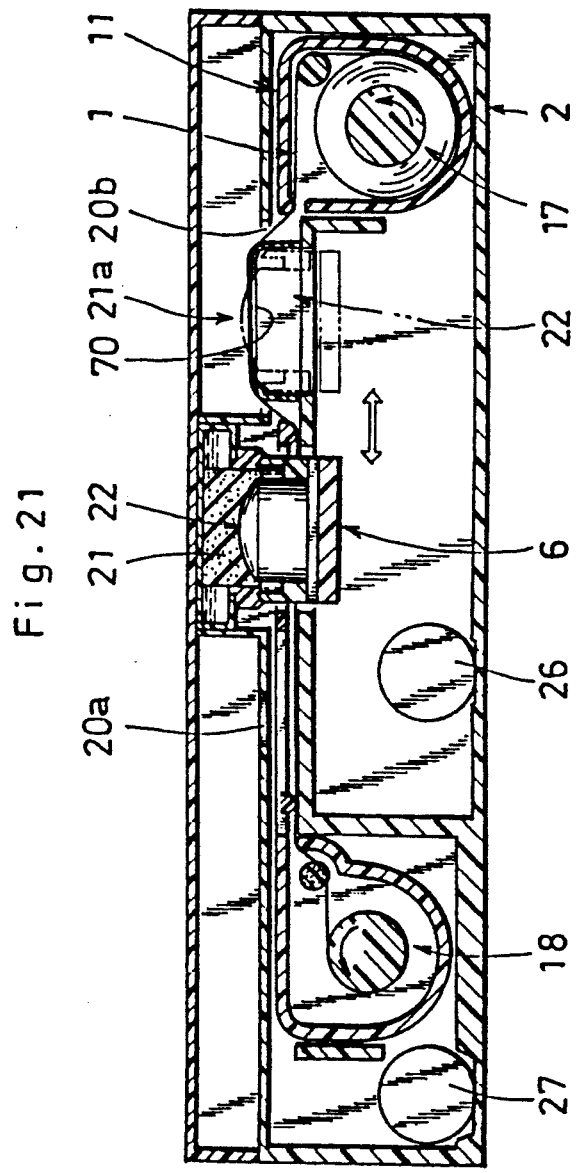
FIG. 21 is a vertical section view of a test apparatus for measuring concentration of a test substance in liquid in accordance with a fifth embodiment of the present invention.

FIG. 21 is a vertical section view of a test apparatus for measuring concentration of a test substance in liquid in accordance with a fifth embodiment of the present invention.

The fifth embodiment differs from the third embodiment as follows.

(1) A depositing table 70 raised through the opening 20b for deposition, is further provided to the test apparatus casing 2.

(2) The concentration measuring electrode 22 is elevated to contact with the diffusion-limiting membrane 16 positioned on the depositing table 70.

In this embodiment, similar operations as the operations of the third embodiment can be performed. Further, the depositing operation of test solution can be remarkably simplified because the difference of altitude between the top surface of the wetting liquid housing tank 21 and the top surface of the depositing table 70 is remarkably decreased, even when the opening 20b for deposition and the wetting liquid housing tank 21 are close one to the other.

Sixth Embodiment

Figure 22A:
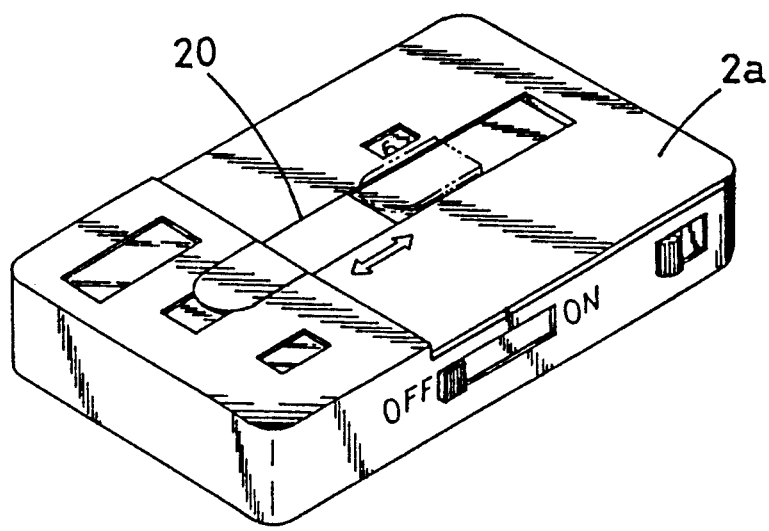
FIG. 22A is a perspective view of a test apparatus for measuring concentration of a test substance in liquid in accordance with a sixth embodiment of the present invention.
Figure 22B:
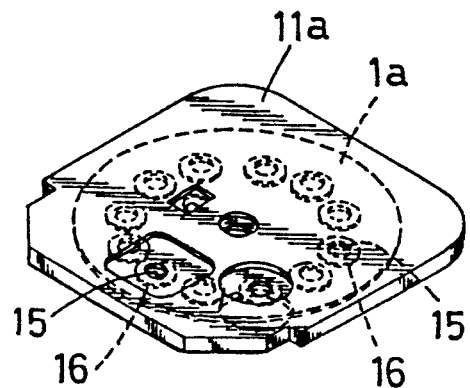
FIG. 22B is a perspective view of a cartridge in which a diffusion-limiting membrane holding member is installed.
Figure 23:
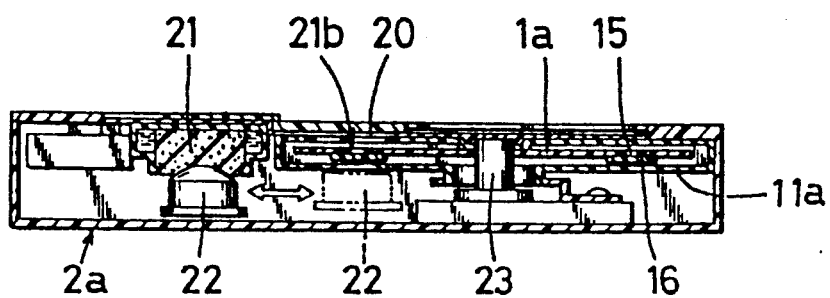
FIG. 23 is a vertical section view of the center portion of the test apparatus in FIG. 22A.

FIG. 22A is a perspective view of a test apparatus for measuring concentration of a test substance in liquid in accordance with a sixth embodiment of the present invention, while FIG. 22B is a perspective view of a catridge in which a diffusion-limiting membrane holding member is installed, and FIG. 23 is a vertical section view of the center portion of the test apparatus in FIG. 22A.

The main point of difference is that a disc shaped thin sheet 1a is housed in a thin catridge 11a instead of the thin elongated sheet 1.

More particularly, a space is formed in a test apparatus casing 2a, for housing the thin cartridge 11a in which the disc shaped thin sheet 1a is housed. An opening 20 for deposition is formed at a predetermined position of the moving path of the disc shaped thin sheet 1a. A wetting liquid housing tank 21 is disposed at a position a little distance apart from a predetermined position which is downward from the opening 20. An electrode driving mechanism (not shown) for moving a concentration measuring electrode 22 between a measuring position for contacting the concentration measuring electrode 22 with the disc shaped thin sheet 1a and a wetting position for contacting the concentration measuring electrode 22 with the wetting liquid housing tank 21, is disposed in the test apparatus casing 2a. The measuring position is a predetermined position downstream from the opening 20. The electrode driving mechanism has an arrangement similar to the electrode driving mechanism illustrated in FIGS. 11 to 13, and detailed description is accordingly omitted. A rotary shaft 23 for rotating the disc shaped thin sheet 1a, is provided in the test apparatus casing 2a and is driven by a motor (not shown). The disc shaped thin sheet 1a has a plurality of through holes 15 in its peripheral portion and a plurality of diffusion-limiting membranes 16 adhered to the disc shaped thin sheet 1a to cover corresponding through hole 15.

Concentration measuring operation based on test solution is carried out by depositing test solution to the through hole 15 open through the opening 20, and then by rotating the disc shaped thin sheet 1a by a predetermined angle and moving the concentration measuring electrode 22 to contact with the diffusion-limiting membrane 16. Thereafter, the concentration measuring electrode 22 is moved in reverse direction so as to being contacted with the wetting liquid housing tank 21. Then next measurement is able to be carried out.

As is apparent from the foregoing, infection resulting from disease germs is securely prevented from occuring even when a test solution is a body fluid. Also, a number of times for installing and disposing of the diffusion-limiting membrane 16 is remarkably decreased.

It is possible in this embodiment that two openings for deposition are formed at different positions one from the other, and it is also possible that a cover member for selectively covering one of two openings, is provided at the test apparatus casing 2a.

In each embodiment, it is possible that the positioning holes 13 and 13a and the end detecting hole 14 are ommited by counting the number of times of performing concentration measuring operation. It is also possible that positioning of the openings 15 and 15a are performed by controlling the rotation angle of the motor because the distance between the openings 15 and 15a is previously determined. It is further possible that a leading edge detecting hole is further provided in the thin sheet.

It is a matter of course that the apparatuses in accordance with the present invention may be applied to apparatuses for measuring a variety of liquids; e.g. cholesterol, neural fat, urine or the like and biological fluids.

Various modifications and applications may occur to those skilled in the art without departing from the spirit and scope of the invention as defined by the appended claims.

What is claimed is:

1. A test apparatus for measuring a concentration of a test substance in a liquid, comprising:
    a cartridge for housing a diffusion-limiting membrane holding member, said holding member including a thin sheet in which through holes for penetrating test solution therethrough are formed at every predetermined distance, and diffusion-limiting membranes are adhered to said thin sheet to cover corresponding through holes, said holding member being movable in a predetermined direction;
    a casing for housing said cartridge therein in a removable manner;
    a concentration measuring electrode provided within said casing;
    first depositing portion means for depositing test solution onto one of said membranes covering one of said through holes, said first depositing portion means being formed at an upper portion of said casing and at an upstream portion in a thin sheet moving direction; and
    concentration measuring portion means for contacting said concentration measuring electrode with a diffusion-limiting membrane, said concentration measuring portion means being formed at an upper portion of said casing and at a downstream portion in the thin sheet moving direction, said concentration measuring portion means being apart by a predetermined distance from said depositing portion means in the thin sheet moving direction.

2. A test apparatus as set forth in claim 1, further comprising a sheet driving means for moving the thin sheet in one direction.

3. A test apparatus as set forth in claim 1, further comprising a sheet driving means for moving the thin sheet to and fro in a predetermined direction.

4. A test apparatus as set forth in claim 1, wherein said depositing portion means includes a larger opening than the through hole, and said depositing portion means and said concentration measuring portion means are apart one from the other by the distance between neighboring through holes.

5. A test apparatus as set forth in claim 1, further comprising a second depositing portion means formed at the upper portion of said casing, said first and second depositing portion means being apart one from the other by a predetermined distance, and a cover means for selectively covering said first and second depositing portion means.

6. A test apparatus as set forth in claim 5, wherein said cover means includes an opening smaller than an opening in said first or second depositing portion means, the smaller opening being formed at a predetermined position in said cover means, said smaller opening being able to be located opposite to one of said through holes.

7. A test apparatus as set forth in claim 1, further comprising a second depositing portion means formed at the upper portion of said casing, said first and second depositing portion means being apart one from the other by a predetermined distance, and a lighting device disposed below an elongated sheet opposite to one of said depositing portion means.

8. A test apparatus as set forth in claim 1, further comprising electrode driving means for moving said concentration measuring electrode to and fro on a plane which is parallel to a moving plane of the thin sheet and for moving said concentration measuring electrode upward and downward when said concentration measuring electrode is moved to a limit on the plane.

9. A test apparatus as set forth in claim 8, further comprising a wetting liquid housing member opposite to said concentration measuring electrode when said concentration measuring electrode moves to a position not opposite to said measuring portion means.

10. A test apparatus as set forth in claim 9, wherein said electrode driving means moves said concentration measuring electrode to and fro in a direction which is not parallel to a moving direction of said thin sheet on the plane.

11. A test apparatus as set forth in claim 9, wherein said electrode driving means moves said concentration measuring electrode to and fro in a direction which is parallel to a moving direction of said thin sheet on the plane.

12. A test apparatus for measuring a concentration of a test substance in a liquid, comprising:
 a cartridge for housing a diffusion-limiting membrane holding member, said holding member including a thin sheet in which through holes for penetrating test solution therethrough are formed at every predetermined distance, and diffusion-limiting membranes are adhered to said thin sheet to cover corresponding through holes, said holding member being movable in a predetermined direction;
 a casing for housing said cartridge therein in a removable manner;
 a concentration measuring electrode provided within said casing;
 a first opening for depositing test solution onto one of said membranes covering one of said through holes, said first opening being formed at an upstream portion of said cartridge in a thin sheet moving direction; and
 a second opening for contacting said concentration measuring electrode with a diffusion-limiting membranes, said second opening being formed at a downstream portion of said cartridge in the thin sheet moving direction, and being apart by a predetermined distance from said opening in the thin sheet moving direction.

* * * * *